US012616705B2

(12) United States Patent
Guy et al.

(10) Patent No.: US 12,616,705 B2
(45) **Date of Patent: *May 5, 2026**

(54) USE OF CANNABINOIDS IN THE TREATMENT OF ANGELMAN SYNDROME

(71) Applicant: JAZZ PHARMACEUTICALS RESEARCH UK LIMITED, Sittingbourne (GB)

(72) Inventors: Geoffrey Guy, Sittingbourne (GB); Stephen Wright, Sittingbourne (GB); James Brodie, Sittingbourne (GB); Marie Woolley-Roberts, Sittingbourne (GB); Livio Luongo, Naples (IT)

(73) Assignee: JAZZ PHARMACEUTICALS RESEARCH UK LIMITED, Sittingbourne (GB)

( * ) Notice: Subject to any disclaimer, the term of this patent is extended or adjusted under 35 U.S.C. 154(b) by 72 days.

This patent is subject to a terminal disclaimer.

(21) Appl. No.: 18/311,221

(22) Filed: May 2, 2023

(65) Prior Publication Data

US 2023/0263744 A1 Aug. 24, 2023

Related U.S. Application Data

(63) Continuation of application No. 16/467,639, filed as application No. PCT/GB2017/053735 on Dec. 13, 2017, now Pat. No. 11,679,087.

(30) Foreign Application Priority Data

Dec. 16, 2016 (GB) ..................................... 1621480

(51) Int. Cl.

| | |
|---|---|
| ***A61K 31/00*** | (2006.01) |
| ***A61K 36/185*** | (2006.01) |
| ***A61K 45/06*** | (2006.01) |
| ***A61P 25/20*** | (2006.01) |

(52) U.S. Cl.

CPC ........ *A61K 31/658* (2023.05); *A61K 36/3482* (2024.05); *A61K 45/06* (2013.01); *A61P 25/20* (2018.01)

(58) Field of Classification Search

CPC ...... A61K 31/05; A61K 36/185; A61K 45/06; A61K 31/192; A61P 25/20; A61P 25/00

See application file for complete search history.

(56) References Cited

U.S. PATENT DOCUMENTS

| | | | |
|---|---|---|---|
| 6,403,126 | B1 | 6/2002 | Webster |
| 6,949,582 | B1 | 9/2005 | Wallace |
| 8,293,786 | B2 | 10/2012 | Stinchcomb |
| 8,632,825 | B2 | 1/2014 | Velasco Diez et al. |
| 8,673,368 | B2 | 3/2014 | Guy et al. |
| 8,790,719 | B2 | 7/2014 | Parolaro et al. |
| 9,017,737 | B2 | 4/2015 | Kikuchi et al. |
| 9,023,322 | B2 | 5/2015 | Van Damme et al. |
| 9,066,920 | B2 | 6/2015 | Whalley et al. |
| 9,095,554 | B2 | 8/2015 | Lewis et al. |
| 9,125,859 | B2 | 9/2015 | Whalley et al. |
| 9,168,278 | B2 | 10/2015 | Guy et al. |
| 9,259,449 | B2 | 2/2016 | Raderman |
| 9,474,726 | B2 | 10/2016 | Guy et al. |
| 9,522,123 | B2 | 12/2016 | Whalley et al. |
| 9,675,654 | B2 | 6/2017 | Parolaro et al. |
| 9,730,911 | B2 | 8/2017 | Verzura et al. |

(Continued)

FOREIGN PATENT DOCUMENTS

| | | |
|---|---|---|
| CA | 2737447 A1 | 10/2012 |
| CA | 2859934 A1 | 3/2016 |

(Continued)

OTHER PUBLICATIONS

Noonan, "How Medical Marijuana's Chemicals May Protect Cells", Scientific American, pp. 1-8, 2015.*

(Continued)

*Primary Examiner* — Sahar Javanmard
(74) *Attorney, Agent, or Firm* — COOLEY LLP

(57) ABSTRACT

The present invention relates to the use of cannabidiol (CBD) in the treatment of Angelman syndrome (AS). CBD has been shown to be particularly effective in improving anxiety in rodent models of AS. The CBD is preferably substantially pure. It may take the form of a highly purified extract of cannabis such that the CBD is present at greater than 98% of the total extract (w/w) and the other components of the extract are characterised. Alternatively, the CBD is synthetically produced. Alternatively, the CBD may be used as a botanical drug substance (BDS) from a cannabis plant in which CBD is the predominant cannabinoid. The CBD may also be present in combination with other cannabinoids and non-cannabinoid components such as terpenes. In use the CBD may be used concomitantly with one or more other medicaments. Alternatively, the CBD may be formulated for administration separately, sequentially or simultaneously with one or more medicaments or the combination may be provided in a single dosage form. Where the CBD is formulated for administration separately, sequentially or simultaneously it may be provided as a kit or together with instructions to administer the one or more components in the manner indicated. It may also be used as the sole medication, i.e. as a monotherapy.

15 Claims, 4 Drawing Sheets

(56) References Cited

U.S. PATENT DOCUMENTS 9,949,936 B2 4/2018 Guy et al.
9,949,937 B2 4/2018 Guy et al.
9,956,183 B2 5/2018 Guy et al.
9,956,184 B2 5/2018 Guy et al.
9,956,185 B2 5/2018 Guy et al.
9,956,186 B2 5/2018 Guy et al.
9,962,341 B2 5/2018 Stott et al.
10,039,724 B2 8/2018 Stott et al.
10,092,525 B2 10/2018 Guy et al.
10,098,867 B2 10/2018 Javid et al.
10,111,840 B2 10/2018 Guy et al.
10,137,095 B2 11/2018 Guy et al.
10,220,005 B2 3/2019 Martinez-Orgado
10,226,433 B2 3/2019 DiMarzo et al.
10,583,096 B2 3/2020 Guy et al.
10,603,288 B2 3/2020 Guy et al.
10,709,671 B2 7/2020 Guy et al.
10,709,673 B2 7/2020 Guy et al.
10,709,674 B2 7/2020 Guy et al.
10,729,665 B2 8/2020 Whalley et al.
10,758,514 B2 9/2020 Liu et al.
10,765,643 B2 9/2020 Guy et al.
10,799,467 B2 10/2020 Whalley et al.
10,807,777 B2 10/2020 Whittle
10,849,860 B2 12/2020 Guy et al.
10,918,608 B2 2/2021 Guy et al.
10,966,939 B2 4/2021 Guy et al.
11,000,486 B2 5/2021 Liu et al.
11,065,209 B2 7/2021 Guy et al.
11,065,227 B2 7/2021 Stott et al.
11,096,905 B2 8/2021 Guy et al.
11,147,776 B2 10/2021 Stott et al.
11,147,783 B2 10/2021 Stott et al.
11,154,516 B2 10/2021 Guy et al.
11,154,517 B2 10/2021 Wright et al.
11,160,757 B1 11/2021 Wilkhu et al.
11,160,795 B2 11/2021 Guy et al.
11,207,292 B2 12/2021 Guy et al.
11,229,612 B2 1/2022 Wright et al.
11,291,631 B2 4/2022 Shah
11,311,498 B2 4/2022 Guy et al.
11,318,109 B2 5/2022 Whalley et al.
11,357,741 B2 6/2022 Guy et al.
11,400,055 B2 8/2022 Guy et al.
11,406,623 B2 8/2022 Guy et al.
11,413,266 B2 8/2022 Biro et al.
11,419,829 B2 8/2022 Whalley et al.
11,426,362 B2 8/2022 Wright et al.
11,446,258 B2 9/2022 Guy et al.
11,590,087 B2 2/2023 Guy et al.
11,633,369 B2 4/2023 Guy et al.
11,679,087 B2 6/2023 Guy et al.
11,684,598 B2 6/2023 Stott et al.
11,701,330 B2 7/2023 Guy et al.
2004/0034108 A1 2/2004 Whittle
2004/0049059 A1 3/2004 Mueller
2004/0110828 A1 6/2004 Chowdhury et al.
2005/0042172 A1 2/2005 Whittle
2005/0266108 A1 12/2005 Flockhart et al.
2006/0039959 A1 2/2006 Wessling
2007/0060638 A1 3/2007 Olmstead
2008/0119544 A1 5/2008 Guy et al.
2008/0188461 A1 8/2008 Guan
2009/0264063 A1 10/2009 Tinsley et al.
2009/0306221 A1 12/2009 Guy et al.
2010/0239693 A1 9/2010 Guy et al.
2010/0317729 A1 12/2010 Guy et al.
2011/0028431 A1 2/2011 Zerbe et al.
2011/0038958 A1 2/2011 Kikuchi et al.
2011/0082195 A1 4/2011 Guy et al.
2012/0004251 A1 1/2012 Whalley et al.
2012/0165402 A1 6/2012 Whalley et al.
2012/0183606 A1 7/2012 Bender et al.
2012/0202891 A1 8/2012 Stinchcomb et al.
2012/0270845 A1 10/2012 Bannister
2013/0209483 A1 8/2013 McAllister
2013/0245110 A1 9/2013 Guy et al.
2013/0296398 A1 11/2013 Whalley et al.
2014/0100269 A1 4/2014 Goskonda et al.
2014/0155456 A9 6/2014 Whalley et al.
2014/0243405 A1 8/2014 Whalley et al.
2014/0335208 A1 11/2014 Cawthorne et al.
2014/0343044 A1 11/2014 Ceulemens
2015/0111939 A1 4/2015 Gruening et al.
2015/0181924 A1 7/2015 Llamas
2015/0320698 A1 11/2015 Whalley et al.
2015/0335590 A1 11/2015 Whalley et al.
2015/0343071 A1 12/2015 Vangara et al.
2015/0359755 A1 12/2015 Guy et al.
2015/0359756 A1 12/2015 Guy et al.
2016/0166498 A1 6/2016 Anastassov
2016/0166514 A1 6/2016 Guy et al.
2016/0166515 A1 6/2016 Guy et al.
2016/0220529 A1 8/2016 Guy et al.
2016/0256411 A1 9/2016 Aung-Din
2016/0338974 A1 11/2016 Aung-Din
2017/0007551 A1 1/2017 Guy et al.
2017/0172939 A1 6/2017 Guy et al.
2017/0172940 A1 6/2017 Guy et al.
2017/0172941 A1 6/2017 Guy et al.
2017/0173043 A1 6/2017 Guy et al.
2017/0173044 A1 6/2017 Guy et al.
2017/0181982 A1 6/2017 Guy et al.
2017/0231923 A1 8/2017 Guy et al.
2017/0239193 A1 8/2017 Guy et al.
2017/0246121 A1 8/2017 Guy et al.
2017/0266126 A1 9/2017 Guy et al.
2017/0273913 A1 9/2017 Wilkhu et al.
2018/0071210 A1 3/2018 Wilkhu et al.
2018/0228751 A1 8/2018 Stott et al.
2018/0338931 A1 11/2018 Guy et al.
2019/0083418 A1 3/2019 Guy et al.
2019/0167583 A1 6/2019 Shah
2019/0175547 A1 6/2019 Stott et al.
2019/0314296 A1 10/2019 Wright et al.
2019/0321307 A1 10/2019 Guy et al.
2019/0365667 A1 12/2019 Wright et al.
2020/0138738 A1 5/2020 Guy et al.
2020/0179303 A1 6/2020 Guy et al.
2020/0206153 A1 7/2020 Whalley et al.
2020/0237683 A1 7/2020 Whalley et al.
2020/0297656 A1 9/2020 Guy et al.
2020/0352878 A1 11/2020 Guy et al.
2021/0015789 A1 1/2021 Guy et al.
2021/0052512 A1 2/2021 Guy et al.
2021/0059949 A1 3/2021 Wilkhu et al.
2021/0059960 A1 3/2021 Wilkhu et al.
2021/0059976 A1 3/2021 Wilkhu et al.
2021/0069333 A1 3/2021 Velasco Diez et al.
2021/0100755 A1 4/2021 Whalley et al.
2021/0169824 A1 6/2021 Guy et al.
2021/0177773 A1 6/2021 Guy et al.
2021/0290565 A1 9/2021 Guy et al.
2021/0308072 A1 10/2021 Wright et al.
2021/0330636 A1 10/2021 Guy et al.
2021/0401771 A1 12/2021 Guy et al.
2022/0000800 A1 1/2022 Guy et al.
2022/0008355 A1 1/2022 Guy et al.
2022/0016048 A1 1/2022 Guy et al.
2022/0023232 A1 1/2022 Guy et al.
2022/0040155 A1 2/2022 Guy et al.
2022/0062197 A1 3/2022 Stott et al.
2022/0062211 A1 3/2022 Stott et al.
2022/0087951 A1 3/2022 Guy et al.
2022/0096397 A1 3/2022 Wright et al.
2022/0168266 A1 6/2022 Guy et al.
2022/0183997 A1 6/2022 Guy et al.
2022/0184000 A1 6/2022 Guy et al.
2022/0202738 A1 6/2022 Guy et al.
2022/0211629 A1 7/2022 Wilkhu et al.
2022/0226257 A1 7/2022 Guy et al.
2022/0233495 A1 7/2022 Silcock et al.
2022/0249396 A1 8/2022 Guy et al.
2022/0257529 A1 8/2022 Guy et al.

(56) References Cited

U.S. PATENT DOCUMENTS

| | | | |
|---|---|---|---|
| 2022/0265573 | A1 | 8/2022 | Guy et al. |
| 2022/0378715 | A1 | 12/2022 | Guy et al. |
| 2022/0378738 | A1 | 12/2022 | Guy et al. |
| 2022/0387347 | A1 | 12/2022 | Whalley et al. |
| 2022/0395470 | A1 | 12/2022 | Whalley et al. |
| 2022/0395471 | A1 | 12/2022 | Guy et al. |
| 2023/0000789 | A1 | 1/2023 | Guy et al. |
| 2023/0022487 | A1 | 1/2023 | Guy et al. |
| 2023/0024312 | A1 | 1/2023 | Whalley et al. |
| 2023/0026079 | A1 | 1/2023 | Guy et al. |
| 2023/0032502 | A1 | 2/2023 | Guy et al. |
| 2023/0038423 | A1 | 2/2023 | Silcock et al. |
| 2023/0068885 | A1 | 3/2023 | Guy et al. |
| 2023/0143812 | A1 | 5/2023 | Knappertz et al. |
| 2023/0235825 | A1 | 7/2023 | Thompson et al. |
| 2023/0248664 | A1 | 8/2023 | Guy et al. |
| 2023/0263744 | A1 | 8/2023 | Guy et al. |

FOREIGN PATENT DOCUMENTS

| | | | |
|---|---|---|---|
| CN | 101040855 | A | 9/2007 |
| CN | 103110582 | A | 5/2013 |
| DE | 10 2012 105 063 | A1 | 12/2013 |
| EP | 2 448 637 | B1 | 5/2012 |
| GB | 2384707 | A | 8/2003 |
| GB | 2434097 | A | 7/2007 |
| GB | 2434312 | A | 7/2007 |
| GB | 2450753 | A | 1/2009 |
| GB | 2456183 | A | 7/2009 |
| GB | 2471523 | A | 1/2011 |
| GB | 2478595 | A | 9/2011 |
| GB | 2479153 | A | 10/2011 |
| GB | 2471565 | B | 7/2012 |
| GB | 2478072 | B | 12/2012 |
| GB | 2478074 | B | 12/2012 |
| GB | 2492487 | A | 1/2013 |
| GB | 2487712 | A | 10/2015 |
| GB | 2531282 | A | 4/2016 |
| GB | 2438682 | A | 12/2017 |
| WO | WO 2002/064109 | A2 | 8/2002 |
| WO | WO 2003/099302 | A1 | 12/2003 |
| WO | WO 2004/016246 | A1 | 2/2004 |
| WO | WO 2004/016277 | A2 | 2/2004 |
| WO | WO 2006/054057 | A2 | 5/2006 |
| WO | WO 2006/133941 | A2 | 12/2006 |
| WO | WO 2007/083098 | A1 | 7/2007 |
| WO | WO 2007/138322 | A1 | 12/2007 |
| WO | WO 2008/019146 | A2 | 2/2008 |
| WO | WO 2008/094181 | A3 | 8/2008 |
| WO | WO 2008/129258 | A1 | 10/2008 |
| WO | WO 2008/144475 | A1 | 11/2008 |
| WO | WO 2008/021394 | A2 | 12/2008 |
| WO | WO 2008/146006 | A1 | 12/2008 |
| WO | WO 2009/007697 | A1 | 1/2009 |
| WO | WO 2009/007698 | A1 | 1/2009 |
| WO | WO 2009/020666 | A1 | 2/2009 |
| WO | WO 2010/012506 | A1 | 2/2010 |
| WO | WO 2011/001169 | A1 | 1/2011 |
| WO | WO 2011/121351 | A1 | 10/2011 |
| WO | WO 2012/033478 | A1 | 3/2012 |
| WO | WO 2012/093255 | A1 | 7/2012 |
| WO | WO 2013/032351 | A1 | 3/2013 |
| WO | WO 2014/146699 | A1 | 9/2014 |
| WO | WO 2015/142501 | A1 | 9/2015 |
| WO | WO 2015/184127 | A2 | 12/2015 |
| WO | WO 2015/193667 | A1 | 12/2015 |
| WO | WO 2015/193668 | A1 | 12/2015 |
| WO | WO 2016/059405 | A1 | 4/2016 |
| WO | WO 2016/084075 | A1 | 6/2016 |
| WO | WO 2016/118391 | A1 | 7/2016 |
| WO | WO 2016/147186 | A1 | 9/2016 |
| WO | WO 2016/022936 | A1 | 11/2016 |
| WO | WO 2016/199148 | A1 | 12/2016 |
| WO | WO 2017/168138 | A1 | 10/2017 |
| WO | WO 2018/002636 | A1 | 1/2018 |
| WO | WO 2018/002637 | A1 | 1/2018 |
| WO | WO 2018/037203 | A1 | 3/2018 |

OTHER PUBLICATIONS

U.S. Appl. No. 15/640,033, filed Jun. 30, 2017.
U.S. Appl. No. 16/768,241, filed May 29, 2020.
U.S. Appl. No. 16/959,350, filed Jun. 30, 2020.
U.S. Appl. No. 16/959,354, filed Jun. 30, 2020.
U.S. Appl. No. 16/959,357, filed Jun. 30, 2020.
U.S. Appl. No. 16/935,005, filed Jul. 21, 2020.
U.S. Appl. No. 17/012,448, filed Sep. 4, 2020.
U.S. Appl. No. 17/050,956, filed Oct. 27, 2020.
U.S. Appl. No. 17/102,109, filed Nov. 23, 2020.
U.S. Appl. No. 17/231,625, filed Apr. 15, 2021.
U.S. Appl. No. 17/296,066, filed May 21, 2021.
U.S. Appl. No. 17/296,076, filed May 21, 2021.
U.S. Appl. No. 17/424,682, filed Jul. 21, 2021.
U.S. Appl. No. 17/426,442, filed Jul. 28, 2021.
U.S. Appl. No. 17/406,401, filed Aug. 19, 2021.
U.S. Appl. No. 17/435,892, filed Sep. 2, 2021.
U.S. Appl. No. 17/472,000, filed Sep. 10, 2021.
U.S. Appl. No. 17/548,232, filed Dec. 10, 2021.
U.S. Appl. No. 17/606,370, filed Oct. 25, 2021.
U.S. Appl. No. 17/611,824, filed Nov. 16, 2021.
U.S. Appl. No. 17/529,005, filed Nov. 17, 2021.
U.S. Appl. No. 17/615,422, filed Nov. 30, 2021.
U.S. Appl. No. 17/552,487, filed Dec. 16, 2021.
U.S. Appl. No. 17/576,868, filed Jan. 14, 2022.
U.S. Appl. No. 17/585,485, filed Jan. 26, 2022.
U.S. Appl. No. 17/627,946, filed Jan. 18, 2022.
U.S. Appl. No. 17/631,069, filed Jan. 28, 2022.
U.S. Appl. No. 17/638,629, filed Feb. 25, 2022.
U.S. Appl. No. 17/689,607, filed Mar. 8, 2022.
U.S. Appl. No. 17/689,245, filed Mar. 8, 2022.
U.S. Appl. No. 17/744,224, filed May 13, 2022.
U.S. Appl. No. 17/705,443, filed Mar. 28, 2022.
U.S. Appl. No. 17/768,048, filed Apr. 11, 2022.
U.S. Appl. No. 17/770,435, filed Apr. 20, 2022.
U.S. Appl. No. 17/770,436, filed Apr. 20, 2022.
U.S. Appl. No. 17/771,184, filed Apr. 22, 2022.
U.S. Appl. No. 17/771,190, filed Apr. 22, 2022.
U.S. Appl. No. 17/771,195, filed Apr. 22, 2022.
U.S. Appl. No. 17/771,183, filed Apr. 22, 2022.
U.S. Appl. No. 17/777,734, filed May 18, 2022.
U.S. Appl. No. 17/777,677, filed May 18, 2022.
U.S. Appl. No. 17/777,681, filed May 18, 2022.
U.S. Appl. No. 17/841,167, filed Jun. 15, 2022.
U.S. Appl. No. 17/786,949, filed Jun. 17, 2022.
U.S. Appl. No. 17/817,753, filed Aug. 5, 2022.
U.S. Appl. No. 17/853,367, filed Jun. 29, 2022.
U.S. Appl. No. 18/002,437, filed Dec. 19, 2022.
U.S. Appl. No. 18/005,838, filed Jan. 17, 2023.
U.S. Appl. No. 18/005,841, filed Jan. 17, 2023.
U.S. Appl. No. 18/005,845, filed Jan. 17, 2023.
U.S. Appl. No. 18/005,843, filed Jan. 17, 2023.
U.S. Appl. No. 18/005,847, filed Jan. 17, 2023.
U.S. Appl. No. 18/005,848, filed Jan. 17, 2023.
U.S. Appl. No. 18/005,851, filed Jan. 18, 2023.
U.S. Appl. No. 18/005,852, filed Jan. 18, 2023.
U.S. Appl. No. 18/005,853, filed Jan. 18, 2023.
U.S. Appl. No. 18/005,959, filed Jan. 18, 2023.
U.S. Appl. No. 18/005,960, filed Jan. 18, 2023.
U.S. Appl. No. 18/005,961, filed Jan. 18, 2023.
U.S. Appl. No. 18/006,125, filed Jan. 19, 2023.
U.S. Appl. No. 18/006,127, filed Jan. 19, 2023.
U.S. Appl. No. 18/006,129, filed Jan. 19, 2023.
U.S. Appl. No. 18/006,131, filed Jan. 19, 2023.
U.S. Appl. No. 18/006,133, filed Jan. 19, 2023.
U.S. Appl. No. 18/006,121, filed Jan. 19, 2023.
U.S. Appl. No. 18/161,603, filed Jan. 30, 2023.

(56) References Cited

OTHER PUBLICATIONS

U.S. Appl. No. 18/170,235, filed Feb. 16, 2023.
U.S. Appl. No. 18/043,810, filed Mar. 2, 2023.
U.S. Appl. No. 18/044,941, filed Mar. 10, 2023.
U.S. Appl. No. 18/245,856, filed Mar. 17, 2023.
U.S. Appl. No. 18/186,792, filed Mar. 20, 2023.
U.S. Appl. No. 18/320,906, filed May 19, 2023.
U.S. Appl. No. 18/256,307, filed Jun. 7, 2023.
U.S. Appl. No. 18/257,373, filed Jun. 14, 2023.
U.S. Appl. No. 18/257,537, filed Jun. 14, 2023.
U.S. Appl. No. 18/257,479, filed Jun. 14, 2023.
U.S. Appl. No. 18/258,485, filed Jun. 20, 2023.
U.S. Appl. No. 18/446,405, filed Aug. 8, 2023.
U.S. Appl. No. 18/546,254, filed Aug. 11, 2023.
U.S. Appl. No. 18/548,003, filed Aug. 25, 2023.
[No Author Listed] "Cannabidiol Therapy for Aicardi Syndrome" Aug. 2014, 4 pages.
[No Author Listed], "Missouri House passes cannabis extract legislation," Kansas City Star, 2014, https://kansascity.com/news/politics-government/article346747.html, 2 pages.
Alger, B. E., "Not too excited? Thank your endocannabinoids," Neuron, 51(4):393-595 (2006).
American Epilepsy Society, Three Studies Shed New Light on the Effectiveness of Cannabis in Epilepsy, Oct. 14, 2014, 2 pages.
Ames, F. R. et al., "Anticonvulsant effect of cannabidiol," S Afr Med J. Jan. 4, 1986; 69(1):14, 1 page.
Arain, A. M., "Pregabalin in the management of partial epilepsy," Neuropsychiatr Dis Treat., 407-13 (2009); Epub Aug. 20, 2009.
Arslan, A. & Tirnaksiz, F., "Self-emulsifying Drug Delivery Systems," F ABAD J Pharm Sci, 38(1):55-64 (2013).
Arzimanoglou et al., "All children who experience epileptic falls do not necessarily have Lennox-Gastaut syndrome . . . but many do," Epileptic Disord. 2011, 13: S3-S13 (2011).
AU Re-examination report—standard patent for Australian Patent No. 2012204800, dated May 3, 2019.
Avoli, M. et al., "Cellular and molecular mechanisms of epilepsy in the human brain," Prog Neurobiol., 77(3):166-200 (2005).
Bakhsm, "Key Attributes of TKDL," Miftaah-al-Khazin, 1930, 607-608, with English Translation, 4 pages.
Bancaud, et al., "Proposal for Revised Clinical and Electroencephalographic Classification of Epileptic Seizures," Epilepsia, 22(4):489-501 (1981).
Banerjee et al., "Case Report: Aicardi syndrome: A report of five Indian cases," Neurology India, 54(1):91-93 (2006).
Barker-Haliski, M. et al., "How Clinical Development Can, and Should Inform Translational Science," Neuron, 84:582-593 (2014).
Benowitz, N. L. et al., "Metabolic and Psychophysiologic studies of cannabidiol hexobarbital interaction," Clin Pharmacol Ther., 28(1):115-120 (1980).
Benowitz & Jones, "Cardiovascular and metabolic considerations in prolonged cannabinoid administration in man," J Clin Pharm, 21:214S-223S, 1981.
Bertram, E., "The Relevance of Kindling for Human Epilepsy," Epilepsia, 48(Suppl. 2):65-74 (2007).
Bhatt, V. P. & Vashishtha, D. P., "Indigenous plants in traditional healthcare system in Kedarnath valley of western Himalaya," Indian J Tradit Knowl., 7(2):300-310 (2000).
Bhattacharyya, S. et al., "Modulation of mediotemporal and ventrostriatal function in humans by Delta9-tetrahydrocannabinol: a neural basis for the effects of *Cannabis sativa* on learning and psychosis," Arch Gen Psychiatry, 66(4):442-451 (2009); doi:10.1001/archgenpsychiatry.2009 .17.
Bipolar Health Group (Charlotte's Web Hemp Remedy, available online at http:/bipolarhealthgroup.org/index.php/charlottes-web-hemp-remedy/, accessed Sep. 6, 2017, 6 pages.
Booth, "Legalization's opening of medical pot research is dream and nightmare," Denver Post, Dec. 14, 2013, http://www.denverpost.com/ci_24726291/legalizations-opening-medical-pot-research-is-dream-and, 6 pages.
Bostanci, M. O. & Bagirici, F., "The effects of octanol on penicillin induced epileptiform activity in rats: an in vivo study," Epilepsy Research, 71:188-194 (2006).
Braida, D. et al., "Post-ischemic treatment with cannabidiol prevents electroencephalographic flattening, hyperlocomotion and neuronal injury in gerbils," Neuroscience Letters., 346:61-64 (2003).
Brust, J. C. M. et al., "Marijuana use and the risk of new onset seizures," Trans Am Clin Climatol Assoc., 103:176-181 (1992).
Carlini, et al., "Hypnotic and antiepileptic effects of cannabidiol," J Clin Pharmacol. Aug.-Sep. 1981;21(8-9 Suppl):417S-427S. Medline abstract only.
Castel-Branco, et al., "The Maximal Electroshock Seizure (MES) Model in the Preclinical 98. Assessment of Potential New Anti epileptic Drugs," Methods Find Exp Clin Pharmacol., 31(2): 101-106 (2009).
cdc.gov [online], "2 to 20 years: Girls Stature-for-age and Weight-for-age percentiles," National Center for Health Statistics and National Center for Chronic Disease Prevention and Health Promotion, last modified Nov. 2000, https://www.cdc.gov/growthcharts/data/set1clinical/cj411022.pdf, 1 page.
Charlotte's Web [ online], "Whole-Plant Cannabinoids Outperform Single Molecule Compounds," CWHemp.com, Jan. 11, 2017, retrieved on Jun. 16, 2017, URL https://www.cwhemp.com/blog/whole-plant-cw-hemp-cannabinoids, 6 pages.
ChildNeurologyFoundation.org [online], "Disorder directory: Learn from the Experts—LGS (Lennon-Gastaut Syndrome)," Child Neurology Foundation, available on or before Sep. 6, 2005, retrieved on May 21, 2018, URL http://www.childneurologyfoundation.org/disorders/lgs-lennox-gastaut-syndrome, 10 pages.
Chiron, C. & Dulac, O., "The Pharmacologic Treatment of Dravet Syndrome," Epilepsia, 52 (Suppl. 2):72-75 (2011).
Chiu, P. et al., "The Influence of Cannabidiol and Δ-Tetrahydrocannabinol on Cobalt Epilepsy in Rats," Epilepsia, 20:365-375 (1979).
Chou, "Theoretical basis, experimental design, and computerized simulation of synergism and antagonism in drug combination studies," Pharmacol Rev, 58(3):621-681 (2006).
Conry, J. A. et al., "Clobazam in the treatment of Lennox-Gastaut syndrome," Epilepsia, 50:1158-1166 (2009).
Consroe, et al. Chapter 12, "Potential Role of Cannabinoids for Therapy of Neurological Disorders." p. 459 in Marijuana Cannabinoids: Neurobiology and Neurophysiology, ed. L. Murphy (1992), 72 pages.
Consroe, et al., "Anticonvulsant drug antagonism of delta9tetrahydrocannabinol-induced seizures in rabbits," Res Commun Chem Pathol Pharmacol., 16(1):1-13 (1977).
Consroe, et al., "Anticonvulsant interaction of cannabidiol and ethosuximide in rats," J Pharm Pharmacol., 29(8):500-501 (1977); doi: 10.1111/j.2042-7158.1977.tb11378.x.
Consroe, et al., "Anticonvulsant nature of marihuana smoking," JAMA, 234(3):306-307 (1975).
Consroe, et al., "Cannabidiol—antiepileptic drug comparisons and interactions in experimentally induced seizures in rats," J Pharmacol Exp Ther., 201(1):26-32 (1977).
Consroe, et al., "Controlled clinical trial of cannabidiol in Huntington's Disease," Pharmacology Biochemistry & Behavior, 40:701-708 (1991).
Consroe, et al., "Effects of cannabidiol on behavioral seizures caused by convulsant drugs or current in mice," Eur J Pharmacol., 83(3-4):293-298 (1982).
Consroe et al,. "Chapter 2: Therapeutic Potential of Cannabinoids in Neurological Disorders," Cannabinoids as Therapeutic Agents, R. Mechoulam, Ed., 1986, pp. 21-49.
Cortesi, et al., "Potential therapeutical effects of cannabidiol in children with pharmacoresistant epilepsy," Med Hypotheses, 68(4):920-921 2007). Epub Nov. 16, 2006.
Cortez, et al. Chapter 10, "Pharmacologic Models of Generalized Absence Seizures in Rodents," Models of Seizures and Epilepsy, 111-126 (2006).
Crespel, A. et al., "Lennox-Gastaut Syndrome," Chapter 14, in Epileptic Syndromes in Infancy, Childhood, and Adolescence, 5th Edition, 2012, ed. M. Bureau, et al., pp. 189-216.

(56) References Cited

OTHER PUBLICATIONS

Cunha, et al., "Chronic administration of cannabidiol to healthy volunteers and epileptic patients," Pharmacology, 21(3):175-85 (1980).
Curia et al., "The pilocarpine model of temporal lobe epilepsy," J Neuroscience Methods, 172(2-4):143-157 (2008).
Czapinski, et al., "Randomized 36-month comparative study of valproic acid (VPA), phenytoin (PHT), phenobarbital (PB) and carbamazepine (CBZ) efficacy in patients with newly diagnosed epilepsy with partial complex seizures," J Neurolog Sci., 150:S162 (1997).
Dasa, et al. "Brhat Nighantu Ratnakara (Saligramanighantubhusanam)." vol. IV. 1997:170. Sanskrit. Exhibit 5, 5 pages, with English translation.
Davis, et al., "A predominant role for inhibition of the adenylate cyclase/protein kinase. A pathway in ERK activation by cannabinoid receptor 1 in NIE-115 neuroblastoma cells," J Biol Chem., 278(49):48973-80 (2003). Epub Sep. 29, 2003.
Davis, et al., "Antiepileptic action of marijuana-active substances," Federation Proceedings, 8:284-5 (1949).
De Oliveira, et al., "Anticonvulsant activity of β-caryophyllene against pentylenetetrazol-induced seizures," Epilepsy Behav., 56:26-31 (2016); doi: 10.1016/j.yebeh.2015.12.040.
De Meijer, "The Chemical Phenotypes (Chemotypes) of Cannabis," Chapter 5, Handbook of Cannabis, ed. Roger G. Pertwee, pp. 89-110 (2014).
Deshpande, et al., "Cannabinoid CB 1 receptor antagonists cause status epilepticus-like activity in the hippocampal neuronal culture model of acquired epilepsy," Neurosci Lett., 41 I(I):1-6 (2007). Epub Nov. 15, 2006.
Devinsky, et al., "Cannabidiol: Pharmacology and potential therapeutic role in epilepsy and other neuropsychiatric disorders," Epilepsia, 55(6):791-802 (2014).
Devinsky et al., "Cannabidiol in patients with treatment-resistant epilepsy: an open-label interventional trial," The Lancet Neurology, vol. 15, pp. 270-278, Mar. 2016.
Dravet, "The core Dravet syndrome phenotype," Epilepsia, 52 Suppl 2:3-9 (2011); doi: 10.1111/j.1528-1167.2011.02994.x.
Dreifus, et al., "Proposal for Revised Clinical and Electroencephalographic Classification of Epileptic Seizures," Epilepsie., 22:489-501 (1981).
Dulac, "Use of Lamotrigine in Lennox-Gastaut and Related Epilepsy Syndromes," J. Child Neurolog., 12(Supplement 1): S23-S29 (1997).
Eadie, "Shortcomings in the current treatment of epilepsy," Expert Rev Neurother., 12(12):1419-27 (2012).
Eggers, "Temporal lobe epilepsy is a disease of faulty neuronal resonators rather than oscillators, and all seizures are provoked, usually by stress," Med Hypotheses., 69(6):1284-9 (2007).
Elsohly and Gul, "Constituents of Cannabis Sariva," Chapter 1, Handbook of Cannabis, Roger G. Pertwee, Ed., pp. 3-22 (2014).
Engel, "Chapter 1. What should be modeled," in Models Seizure Epilepsy, 2006, 14 pages.
Engel, "Report of the ILAE classification core group," Epilepsia, 47(9):1558-68 (2006).
Epidiolex® (cannabidiol) oral solution, CV, Prescribing Information, 2018, 30 pages; https://www.accessdata.fda.gov/drugsatfda_docs/label/2018/210365lbl.pdf.
EPO Annex to the Communication in Opposition for European Appln. No. 10734541.5, dated Nov. 2, 2016, 45 pages.
EPO Auxiliary Requests to the File in European Patent No. EP2448637, dated Nov. 2, 2016.
EPO Communication of a Notice of Opposition in European Appln. No. 10734541.5, dated Dec. 17, 2014, 1 page.
EPO Communication Pursuant to Article 94(3) EPC in European Appln. No. 10734541.5, dated Oct. 23, 2012, 3 pages.
EPO Interlocutory Decision in Opposition in European Application No. EP2448637, Dec. 15, 2016, 91 pages.
EPO Letter from Opponent Regarding Oral Proceedings in European Patent No. EP2448637, dated Oct. 20, 2016, 6 pages.
EPO Notice of Appeal in European Patent No. EP2448637, dated Feb. 14, 2017, 5 pages.
EPO Notice of Opposition to a European Patent No. EP2448637, dated Dec. 5, 2014, 20 pages.
EPO Opponent Response to the Preliminary Opinion of the Opposition Division in European Patent No. EP2448637, dated Jun. 23, 2016, 27 pages.
EPO Opponent Response to the Preliminary Opinion of the Opposition Division in European Patent No. EP2448637, dated Sep. 9, 2016, 25 pages.
EPO Opponent Response to the Written Submissions in European Patent No. EP2448637, dated Oct. 12, 2016, 18 pages.
EPO Opponent Response to the written Submissions in European Patent No. EP2448637, dated Oct. 20, 2016, 3 pages.
EPO Opponent Written Submission in European Patent No. EP2448637, dated Nov. 4, 2016, 3 pages.
EPO Opposition, Expert Statement of Dr. Emma Louise Cheetham in European Appln. No. EP10734541.5, dated Nov. 4, 2016, 1 page.
EPO Opposition, Expert Statement of Professor Anthony G. Marson in European Appln. No. EP10734541.5, dated Jun. 14, 2016, 9 pages.
EPO Opposition, Expert Statement of Benjamin J. Whalley in European Appln. No. EP10734541.5, dated Sep. 9, 2016, 11 pages.
EPO Opposition, Expert Statement of Vincenzo Di Marzo in European Appln. No. EP10734541.5, dated Sep. 9, 2016, 10 pages.
EPO Opposition, Supplemental Expert Statement of Professor Benjamin J. Whalley, dated Nov. 4, 2016, 9 pages.
EPO Reply of the Patent Proprietor to the Notice(s) of Opposition in European Patent No. 2448637, dated May 28, 2015, 12 pages.
EPO Reply to Examination Report in European Patent Application No. 10734541.5, dated Feb. 15, 2013, 54 pages.
EPO Reply to Opponent's Written Submission in European Patent No. EP2448637, dated Nov. 4, 2016, 13 pages.
EPO Reply to Opponent's Written Submission in European Patent No. EP2448637, dated Oct. 18, 2016, 5 pages.
EPO Reply to Preliminary Opinion and Opponent's Observations in European Patent No. EP2448637, dated Sep. 9, 2016, 65 pages.
EPO Reply to Proprietor's Statement of Grounds of Appeal in European Patent No. EP2448637, Dated Sep. 8, 2017, 5 pages.
EPO Response to the Statement of Grounds of Appeal in European Patent No. EP2448637, dated Sep. 5, 2017, 17 pages.
EPO Statement of Grounds of Appeal in European Appln. No. 10734541.5, dated Apr. 21, 2017, 13 pages.
EPO Statement of Opposition in European Appln. No. 10734541.5, dated Dec. 5, 2014, 14 pages.
EPO Third Party Observations in European Appln. No. 10734541.5, dated Apr. 3, 2017, 19 pages.
EPO Third Party Observations in European Appln. No. 11712658.1, dated Nov. 22, 2013, 14 pages.
Fariello, "Parenteral Penicillin in Rats: An Experimental Model of Multifocal Epilepsy," Epilepsia, 17:217-222 (1976).
FDA [online], "Warning Letters and Test Results for Cannabidiol-Related Products," 2015 Warning Letters, retrieved on Nov. 14, 2017, URL <https://www.fda.gov/newsevents/publichealthfocus/ucm484109.htm>, 4 pages.
FDA [online], "Warning Letters and Test Results for Cannabidiol-Related Products," 2016 Warning Letters, retrieved on Nov. 14, 2017, URL <https://www.fda.gov/newsevents/publichealthfocus/ucm484109.htm>, 4 pages.
FDA, Guidance for Industry: Estimating the maximum Safe Starting Dose in Initial Clinical Trials for Therapeutics in Adult Healthy Volunteers, U.S. Dept of Health and Human Services: Food and Drug Administration, Jul. 2005, 30 pages.
Ferdinand, et al., "Cannabis—psychosis pathway independent of other types of psychopathology," Schizophr Res., 79(2-3):289-295 (2005).
Fisher, et al., "The impact of epilepsy from the patient's perspective I. Descriptions and subjective perceptions," Epilepsy Res.,41(1):39-51 (2000).
Gabor, et al., "Lorazepam versus phenobarbital: Candidates for drug of choice for treatment of status epilepticus," J Epilepsy, 3(1):3-6 (1990).

(56) References Cited

OTHER PUBLICATIONS

Gallily, et al., "Overcoming the Bell-Shaped Dose-Response of Cannabidiol by Using Cannabis Extract Enriched in Cannabidiol," Pharmacology & Pharmacy, 6:75-85 (2015).
Gardner [online], "Comes Now Epidiolex (FDA Approves IND Studies of CBD)," BeyondTHC.com, Oct. 22, 2013, retrieved on Jan. 31, 2018, http://www.beyondthc.com/comes-now-epidiolex-fda-approves-ind-studies-of-cbd, 4 pages.
Gastaut, "Clinical and electroencephalographical classification of epileptic seizures," Epilepsia, 10: Suppl:2-13 (1969).
Combined Search and Examination Report mailed Jan. 4, 2012 for Application No. GB 1116789.7, 8 pages.
Combined Search and Examination Report for GB Application No. GB1611544.6, dated Mar. 29, 2017, 8 pages.
Combined Search and Examination Report mailed Mar. 25, 2011, for Application No. GB 1100043.7, 8 pages.
Combined Search and Examination Report Under Sections 17 and 18 (3) for International Application No. GB1121919.3, dated Feb. 29, 2012, 8 pages.
Combined Search and Examination Report Under Sections 17 and 18 (3) for International Application No. GB 141077 1.8, dated Feb. 27, 2018, 7 pages.
Combined Search and Examination Report mailed Sep. 5, 2014, for Application No. GB 1414813.4, 8 pages.
Combined Search and Examination Report Under Sections 17 and 18 (3) for International Application No. GB 1418170.5, dated Jul. 2, 2015, 8 pages.
Combined Search and Examination Report Under Sections 17 and 18 (3) for International Application No. GB 1418166.3, dated Jul. 2, 2015, 8 pages.
Combined Search and Examination Report Under Sections 17 and 18 (3) for International Application No. GB 1418171.3, dated Jun. 29, 2015, 8 pages.
Combined Search and Examination Report Under Sections 17 and 18 (3) for International Application No. GB 1506550.1, dated Feb. 5, 2016, 9 pages.
Combined Search and Examination Report for GB Application No. GB1514079.1, dated May 4, 2016, 9 pages.
Combined Search and Examination Report for GB Application No. GB160544.8, dated Jan. 12, 2017, 6 pages.
Combined Search and Examination Report for GB Application No. GB1621480.1, dated Sep. 22, 2017, 7 pages.
GB Examination Report in GB Appln. No. GB1100043.7, dated Mar. 18, 2014, 2 pages.
Gedde [online], "Clinical Experience with Cannabis in Treatment-Resistant Pediatric Epilepsy," Marijuana for Medical Professionals Conference, Sep. 9-11, 2014, URL <http://www.theroc.us/images/gedde_presentation.pdf, Sep. 9-11, 2014>, 45 pages.
Gedde et al., "3.330: Whole Cannabis Extract of High Concentration Cannabidiol May Calm Seizures in Highly Refractory Pediatric Epilepsies," American Epilepsy Society, Dec. 2013, 449-450.
Geffrey et al. "Cannabidiol (CBD) Treatment for Refractory Epilepsy," American Epilepsy Society, Annual Meeting Abstract 2.427, 2014, retrieved on Feb. 10, 2017, URL <https://www.aesnet.org/meetings_events/annual_meeting_abstracts/view/1868979>, 2 pages.
Green, "CBD: An Unconventional Therapy," available online at http://nugs.com/article/cbd-anunconventional-therapy.html, published Mar. 24, 2014, 5 pages.
Gresham, et al., "Treating Lennox-Gastaut syndrome in epileptic pediatric patients with third generation rufinamide," Neuropsychiatr Dis Treat., 6:639-645 (2010).
Gross, et al., "Marijuana use and epilepsy: prevalence in patients of a tertiary care epilepsy center," Neurology, 62(11 ):2095-7 (2004).
Grotenhermen, "Epilepsiebehandlung des Angelman-Syndromes mit CBD (Cannabidiol) (Epilepsy treatment of Angelman syndrome with CBD (cannabidiol)," Angelman e. V., Jan. 2015, retrieved on Jun. 7, 2019, URL <http://s8a5e4d6fcfb04b6.jimcontent.com/download/version/1472724876//module/9873059694/name/Epilepsiebehandlung%20durch%20CBD.pdf> (with Machine English translation), 8 pages.
Guerrini, et al., "Lamotrigine and Seizure Aggravation in Severe Myoclonic Epilepsy," Epilepsia, 39(5):508-512 (1998).
Guimares, et al., "Antianxiety effect of cannabidiol in the elevated plus-maze," Psychopharmacology (Berl)., 100(4):558-9 (1990); doi: 10.1007/BF02244012.
GWPharm [online], "GW Pharmaceuticals Announces Epidiolex(R) Receives Fast Track Designation from FDA for the Treatment of Dravet Syndrome," GW Pharmaceuticals Press Release, Jun. 6, 2014, retrieved on Mar. 1, 2017, URL https://www.gwpharm.com/about-us/news/gw-pharmaceuticals-announces-epidiolex%C2%AE-receives-fast-track-designation-fda-treatment, 2 pages.
GWPharm [online], "GW Pharmaceuticals Announces Physician Reports of Epidiolex(R) Treatment Effect in Children and Young Adults with Treatment-resistant epilepsy from Physician-Led Expanded Access Treatment Program," GW Pharmaceuticals Press Release, Jun. 17, 2014, 8 pages.
GWPharm [online], "GW Pharmaceuticals Announces Preliminary Results of Phase 2a Study for its Pipeline Compound GWP42006," GW Pharmaceuticals Press Release, Feb. 21, 2018, 5 pages.
GWPharm [online], "GW Pharmaceuticals Provides Update on Orphan Program in Childhood Epilepsy for Epidiolex®," GW Pharmaceuticals Press Release, Nov. 15, 2013, 5 pages.
GWPharm [online], "GW Pharmaceuticals Receives Orphan Drug Designation by FDA for Epidiolex® in the treatment of Lennox-Gastaut Syndrome," GW Pharmaceuticals Press Release, Feb. 28, 2014, retrieved on Feb. 10, 2017, URL <https://www.gwpharm.com/about-us/news/gw-pharmaceuticals-receives-orphan-drug-designation-fda-epidiolex%C2%AE-treatment-lennox>, 4 pages.
GWPharm [online], "Orphan Drug Designation Granted for Epidiolex in Dravet syndrome by the FDA—Seven Expanded Access INDs granted by FDA to US physicians to treat with Epidiolex 125 children suffering from intractable epilepsy syndromes," GW Pharmaceuticals Press Release, Nov. 15, 2013, retrieved on Feb. 10, 2017, URL <https://www.gwpharm.com/about-us/news/gw-pharmaceuticals-provides-update-orphan-program-childhood-epilepsy-epidiolex%C2%AE>, 5 pages.
Heinemann et al., "An Overview of in Vitro Seizure Models in Acute and Organotypic Slices," Chapter 4, 35-44 (2006).
Hill et al., "Cannabidivarin is anticonvulsant in mouse and rat," Br J Pharmacol, 167(8):1629-1642 (2012).
Hill et al. "Δ9-Tetrahydrocannabivarin suppresses in vitro epileptiform and in vivo seizure activity in adult rats." Epilepsia. Aug. 2010;51(8):1522-32. doi: 10.1111/j.1528-1167.2010.02523.x. Epub Feb. 26, 2010.
Hill, "Cannabidivarin-rich cannabis extracts are anticonvulsant in mouse and rat via a CB 1 receptor-independent mechanism," British Journal of Pharmacology, Oct. 2013, 170(3): 679-692.
Holmes et al., "Choosing the correct AED: From Animal Studies to the Clinic," Pediatr Neurol. Mar. 2008; 38(3): 151-162.
Annotti et al. "Nonpsychotropic plant cannabinoids, cannabidivarin (CBDV) and cannabidiol (CBD), activate and desensitize transient receptor potential vanilloid 1 (TRPV1) channels in vitro: potential for the treatment of neuronal hyperexcitability." ACS Chem Neurosci. Nov. 19, 2014;5(11):1131-41. doi: 10.1021/cn5000524.
ICE Epilepsy Alliance, the Dravet Syndrome Spectrum, Nov. 2, 2008, 2 pages.
*Insys Development Company, Inc.* v. *GW Pharma Limited and Otsuka Pharmaceutical Co., Ltd.*, Decision in IPR2017-00503, U.S. Pat. No. 9,066,920, dated Jul. 7, 2017, 26 pages.
*Insys Development Company, Inc.* v. *GW Pharma Limited and Otsuka Pharmaceutical Co., Ltd.*, Declaration by Mark Polyakov, IPR2017-00503, U.S. Pat. No. 9,066,920, dated May 29, 2018, 1 page.
*Insys Development Company, Inc.* v. *GW Pharma Limitied and Otsuka Pharmaceutical Co., Ltd.*, Declaration of Professor Anthony G. Marson in IPR2017-00503, U.S. Pat. No. 9,066,920, dated Dec. 13, 2016, 28 pages.
*Insys Development Company, Inc.* v. *GW Pharma Limitied and Otsuka Pharmaceutical Co., Ltd.*, Declaration of Professor Steve White in IPRP2017-00503, U.S. Pat. No. 9,066,920, dated Oct. 24, 2017, 69 pages.

(56) References Cited

OTHER PUBLICATIONS

*Insys Development Company, Inc.* v. *GW Pharma Limitied and Otsuka Pharmaceutical Co., Ltd.*, Declaration of Leslie Benet in IPRP2017-00503, U.S. Pat. No. 9,066,920, dated Nov. 22, 2016, 18 pages.
*Insys Development Company, Inc.* v. *GW Pharma Limitied and Otsuka Pharmaceutical Co., Ltd.*, Declaration of Steve White in IPRP2017-00503, U.S. Pat. No. 9,066,920, dated Dec. 13, 2016, 50 pages.
*Insys Development Company, Inc.* v. *GW Pharma Limitied and Otsuka Pharmaceutical Co., Ltd.*, Final Written Decision in IPRP2017-00503, U.S. Pat. No. 9,066,920, dated Jan. 3, 2019, 40 pages.
*Insys Development Company, Inc.* v. *GW Pharma Limitied and Otsuka Pharmaceutical Co., Ltd.*, Patent Owner's Preliminary Response in IPRP2017-00503, U.S. Pat. No. 9,066,920, dated Apr. 11, 2017, 45 pages.
*Insys Development Company, Inc.* v. *GW Pharma Limitied and Otsuka Pharmaceutical Co., Ltd.*, Petition for Inter Partes Review in IPRP2017-00503, U.S. Pat. No. 9,066,920, dated Dec. 16, 2016, 78 pages.
*Insys Development Company, Inc.* v. *GW Pharma Limitied and Otsuka Pharmaceutical Co., Ltd.*, Petitioner's Brief Regarding Ground III of the IPRP2017-00503, U.S. Pat. No. 9,066,920, dated May 29, 2018, 45 pages.
*Insys Development Company, Inc.* v. *GW Pharma Limitied and Otsuka Pharmaceutical Co., Ltd.*, Petitioner's Reply to Patent Owner's Response in IPRP2017-00503, U.S. Pat. No. 9,066,920, dated Jun. 19, 2018, 6 pages.
*Insys Development Company, Inc.* v. *GW Pharma Limitied and Otsuka Pharmaceutical Co., Ltd.*, Petitioner's Reply to Response in IPRP2017-00503, U.S. Pat. No. 9,066,920, dated Jan. 19, 2018, 36 pages.
IUPHAR/BPS Guide to Pharmacology [online], "Entry for Δ9-tetrahydrocannabidiol," available on or before Mar. 29, 2016, retrieved on Jun. 20, 2018, URL <http://www.guidetopharmacology.org/GRAC/LigandDisplayForward?tab=biology&ligandID=242>, 2 pages.
Iuvone et al., "Neuroprotective effect of cannabidiol, a non-psychoactive component from *Cannabis sativa*, on beta-amyloid-induced toxicity in PC12 cells." J Neurochem. Apr. 2004; 89(1 ): 134-41.
Izzo, et al., "Non-psychotropic plant cannabinoids: new therapeutic opportunities from an ancient herb," Trends in Pharmacological Sciences, 30(10):515-527 (2009).
Jacobson, "Survey of Current Cannabidiol Use in Pediatric Treatment-Resistant Epilepsy," Apr. 22, 2013; https://www.thcint.com/uploads/1/9/3/7/19371199/cannabidiol_use_in_pediatric_epilepsy.pdf, 1 page.
Jeavons, et al., "Sodium valproate in treatment of epilepsy," Br Med J., 2(5919):584-6 (1974).
Jones et al. [online], Info & Metrics / Article Information," Cannabidiol Displays Antiepileptic from and Antiseizure Properties in Vitro and in Vivo," J Pharmacol Exp Ther., Feb. 2010, 332(2): 569-577, retrieved on Jun. 25, 2018, URL: http://jpet.aspetjournals.org/content/332/2/569/tab-article-info.
Jones et al., "Cannabidiol Displays Antiepileptiform and Antiseizure Properties in Vitro and in Vivo," J Pharmacol Exp Ther., 332(2):559-577 (2010).
Joy, et al., "Marijuana and Medicine. Assessing the Science Base," National Academy Press. Washington D.C., 1999, 170 pages.
Kahan, et al., "Risk of selection bias in randomized trials," Trials, 16:405 (2015), 7 pages.
Kaplan, "F.D.A. Panel Recommends Approval of Cannabis-Based Drug for Epilepsy," NY Times, Apr. 19, 2018, retrieved on Jun. 20, 2018, URL <https://www .nytimes.com/2018/04/19/health/epidiolex-fda-cannabis-marajuana.html>, 3 pages.
Karler et al., "The anticonvulsant activity of cannabidiol and cannabinol," Life Science, 13:1527-1531 (1973).
Karler, et al., "The cannabinoids as potential antiepileptics," J Clin Pharmacol, 21(8-9 Suppl):437S-447S (1981).
Kelley, et al., "Doose syndrome (myoclonic-astatic epilepsy): 40 years of progress," Developmental Medicine & Child Neurology, 52:988-993 (2010).
Khan et al., "Key Attributes of TKDL: Laooq-e-Quinnab/Barai Zeequn-Nafs," Khazaain-al-Advia, 1911 (with English translation), 2 pages.
Khan et al., Key Attributes of TKDL: Nushka-e-Qutoor, Muheet-e-Azam, 1887 (with English translation), 2 pages.
Khan et al., "Key Attributes of TKDL: Sufoof-e-Qinnab Barae Waja," Khazaain-al-Adiva, 1911, (with English translation), 5 pages.
Khan et al., "Key Attributes of TKDL: Usaara-e-Qinnab Barai Qoolanj," Khazaain-al-Advia, 1911 (with English translation), 6 pages.
Khan et al., "Key Attributes of TKDL: Zimad-e-Qinnab," Khazaain-al-Adiva, 1911 (with English translation), 5 pages.
Klitgaard, et al., "Electrophysiological, neurochemical and regional effects of levetiracetam in the rat pilocarpine model of temporal lobe epilepsy," Seizure, 12(2):92-100 (2003).
Klitgaard, et al., "Evidence for a unique profile of levetiracetam in rodent models of seizures and epilepsy," European Journal of Pharmacology, 353(2):191-206 (1998).
Kramer, et al., "Febrile infection-related epilepsy syndrome (FIRES): pathogenesis, treatment, and outcome: a multicenter study on 77 children," Epilepsia, 52(11):1956-65 (2011); doi:10.1111/j.1528-1167.2011.03250. x. Epub Aug. 29, 2011.
Kruk-Slomka et al., "A comparison of mecamylamine and bupropion effects on memory-related responses induced by nicotine and scopolamine in the novel object recognition test in mice," Pharmacological Reports, 66(4):638-646 (2014).
Kuhn et al., "Potent activity of carfilzomib, a novel, irreversible inhibitor of the ubiquitin-proteasome pathway, against preclinical models of multiple myeloma," Blood, 110(9):3281-3290 (2007).
Kurz & Blass, "Use of dronabinol (delta-9-THC) in autism: A prospective single-case-study with an early infantile autistic child," Cannabinoids, 5(4):4-6 (2010).
Kwan et al., "Definition of drug resistant epilepsy: consensus proposal by the ad hoc Task Force of the ILAE Commission on Therapeutic Strategies," Epilepsia, 51(6):1069-77 (2010); doi:10.1111/j.1528-1167.2009.02397. x. Epub Nov. 3, 2009. Erratum in: Epilepsia. Sep. 2010;51(9): 1922.
LaPrarie et al., "Cannabidiol is a negative allosteric modulator of the cannabinoid CB1 receptor," British J Pharmacology, 172(20):4790-4805 (2015).
LeafScience.com [online], "What are the Highest CBD Strains?" Oct. 15, 2014, retrieved on Feb. 16, 2017, URL www.leafscience.com/2014/10/15/highest-cbd-strains/, 2 pages.
Leo, et al., "Cannabidiol and epilepsy: Rationale and therapeutic potential," Pharmacological Research, 107:85-92 (2017).
Lewis, "Mystery Mechanisms," The Scientist.com, Jul. 29, 2016, retrieved on Nov. 8, 2017, URL <https://www.the-scientist.com/?articles.view/articleNo/46688/title/Mystery-Mechanisms/>, 2 pages.
Lieu, et al., "Assessment of self-selection bias in a pediatric unilateral hearing loss study," Otolaryngol Head Neck Surg., 142(3):427-433 (2010).
Lindamood and Colasanti, "Effects of delta 9-tetrahydrocannabinol and cannabidiol on sodium-dependent high affinity choline uptake in the rat hippocampus," J Pharmacology Experimental Therapeutics, 213(2):216-221 (1980).
Long, et al., "The pharmacological actions of cannabidiol," Drugs of the Future, 30(7):747-53 (2005).
Loscher and Schmidt, "Modern antiepileptic drug development has failed to deliver: ways out of the current dilemma," Epilepsia, 52(4):657-78 (2011); doi:10.1111/j.1528-1167.2011.03024. x.
Lowenstein, "Chapter 363: Seizures and Epilepsy," Diseases of the Central Nervous System, 2498-2512 (2008).
Luttjohann, et al., "A revised Racine's scale for PTZ-induced seizures in rats," Physiol Behav., 98(5):579-86 (2009); doi: 10.1016/j.physbeh.2009.09.005.
Lutz, "On-demand activation of the endocannabinoid system in the control of neuronal excitability and epileptiform seizures," Biochem Pharmacol., 68(9):1691-8 (2004).
Maa et al., "The case for medical marijuana in epilepsy," Epilepsia, 55(6):783-786 (2014).

(56) References Cited

OTHER PUBLICATIONS

Mackie, "Cannabinoid receptors as therapeutic targets," Annu Rev Pharmacol Toxicol., 46:101-22 (2006).
Majoosi et al., "Key attributes of TKDL: Saoot Baraae Sara," Kaamil-al-Sena'ah, Central Council for Research in Unani Medicine, 2005, with English translation, 2 pages.
Malfait, et al. "The nonpsychoactive cannabis constituent cannabidiol is an oral anti-arthritic therapeutic in murine collagen-induced arthritis," PNAS, 97(17):9561-9566 (2000).
Manni et al., "Obstructive Sleep Apnea in a Clinical Series of Adult Epilepsy Patients: Frequency and Features of the Comorbidity," Epilepsia, 44(6):836-840 (2003).
Manno, "Status Epilepticus: Current Treatment Strategies," The Neurohospitalist, 1(1):23-31 (2011).
Mares et al., "Chapter 12: Electrical Stimulation-Induced Models of Seizures in Model of Seizures and Epilepsy Asla Pitkanen," Philip A. Schwartzkroin & Solomon L. Moshe, eds., 2004, 7 pages.
Martin et al., "Structure-Anticonvulsant Activity Relationships of Cannabidiol Analogs," National Institute on Drug Abuse, Research Monograph Series, 79:48-58 (1987).
Mattson, et al., "Comparison of carbamazepine, phenobarbital, phenytoin, and primidone in partial and secondarily generalized tonic-clonic seizures," N. Engl. J. Med, 313(3):145-151 (1985).
Mattson, et al., "Prognosis for total control of complex partial and secondary generalized tonic clonic seizures," Neurology, 47:68-76 (1996).
Mccormick et al., "On the cellular and network bases of epileptic seizures," Annu Rev Physiol., 63:815-46 (2001).
Mcnamara, "Chapter 19: Pharmacotherapy of the Epilepsies,", Goodman & Gilman's The Pharmacological Basis of Therapeutics 11th ed., McGraw-Hill Companies, pp. 501-525 (2006).
Mechoulam, et al., "Cannabidiol: An Overview of Some Pharmacological Aspects," J Clin Pharmacol, 42:11S-19S (2002).
Mechoulam, et al., Toward drugs derived from cannabis, Naturwissenschaften, 65(4):174-9 (1978).
Medicos [online]. "Convulsive Disorders and their Interference with Driving," Medicos, 2014, retrieved Feb. 10, 2017, URL <https://www.medicosporlaseguridadvial.com/en/clinical-subjects/neurologic-diseases/convulsive-disorders-and-their-interference-with-driving>, 3 pages.
Merlis, "Proposal for an international classification of the epilepsies," Epilepsia, 1(1):114-9 (1970).
Miller, et al., "Mapping genetic modifiers of survival in a mouse model of Dravet syndrome," Genes, Brain and Behavior, 13:163-172 (2014).
Moral, et al., "Pipeline on the Move," Drugs of the Future, 39(1):49-56 (2014).
Morard, et al., "Conversion to Sirolimus-Based Immunosuppression in Maintenance Liver Transplantation Patients," Liver Transplantation, 13:658-664 (2007).
Morelli et al., "The effects of cannabidiol and its synergism with bortezomib in multiple myeloma cell lines. A role for transient receptor potential Vanilloid type-2," Blood, 110(9):3281-3290 (2014).
MyVirtualMedicalCentre [online], "Aicardi syndrome," mymc.com, Feb. 2004, retrieved on Jan. 25, 2019 at https://www.myvmc.com/diseases/aicardi-syndrome/, 6 pages.
Nabissi et al., "Cannabinoids synergize with carfilzomib, reducing multiple myeloma cells viability and migration," Oncotarget, 7:77553 (2016), 15 pages.
Neto, et al., "The role of polar phytocomplexes on anticonvulsant effects of leaf extracts of Lippia Alba (Mill.) N.E. Brown chemotypes," J. Pharm Pharmacol. 61(7):933-9 (2009).
Ng et al., "Illicit drug use and the risk of new-onset seizures." Am J Epidemiol., 132(1):47-57 (1990).
Oakley, et al., "Dravet Syndrome Insights into pathophysiology and therapy from a mouse model of Dravet syndrome," Epilepsia 52(Suppl. 2):59-61 (2011).
Obay et al., "Antiepileptic effects of ghrelin on pentylenetetrazol-induced seizures in rats," Peptides, 28(6):1214-9 (2007). Epub Apr. 19, 2007.
PCT International Preliminary Report on Patentability in International Application No. PCT/GB2010/051066, dated Jun. 9, 2011, 6 pages.
PCT International Preliminary Report on Patentability in International Application No. PCT/GB2012/052284, dated Dec. 12, 2013, 12 pages.
PCT International Preliminary Report on Patentability in International Application No. PCT/GB2015/051775, dated Aug. 10, 2016, 9 pages.
PCT International Preliminary Report on Patentability in International Application No. PCT/GB2015/053030, dated Apr. 18, 2017, 6 pages.
PCT International Preliminary Report on Patentability in International Application No. PCT/GB2016/051792, dated Sep. 1, 2017, 14 pages.
PCT International Preliminary Report on Patentability in International Application No. PCT/GB2017/052229, dated Feb. 26, 2019, 7 pages.
PCT International Preliminary Report on Patentability in International Application No. PCT/US2017/050868, dated Oct. 11, 2018, 7 pages.
PCT International Search Report and Written Opinion in International Application No. PCT/GB2010/051066, dated Dec. 13, 2010, 8 pages.
PCT International Search Report and Written Opinion in International Application No. PCT/GB2011/050649, dated May 30, 2011, 15 pages.
PCT International Search Report and Written Opinion in International Application No. PCT/GB2012/052284, dated Nov. 16, 2012, 11 pages.
PCT International Search Report and Written Opinion in International Application No. PCT/GB2015/051775, dated Aug. 26, 2015, 11 pages.
PCT International Search Report and Written Opinion in International Application No. PCT/GB2015/051776, dated Aug. 25, 2015, 11 pages.
PCT International Search Report and Written Opinion in International Application No. PCT/GB2016/052340, dated Oct. 25, 2016, 12 pages.
PCT International Search Report and Written Opinion in International Application No. PCT/GB2017/051913, dated Sep. 15, 2017, 9 pages.
PCT International Search Report and Written Opinion in International Application No. PCT/GB2017/051914, dated Sep. 12, 2017, 10 pages.
PCT International Search Report and Written Opinion in International Application No. PCT/GB2017/052229, dated Oct. 6, 2017, 10 pages.
PCT International Search Report and Written Opinion in International Application No. PCT/US2017/050868, dated Aug. 6, 2017, 14 pages.
PCT International Search Report and Written Opinion in International Application No. PCT/GB2017/051943, dated Sep. 12, 2017, 10 pages.
PCT International Search Report for PCT/GB2012/050002, dated Feb. 24, 2012, 3 pages.
PCT International Search Report and Written Opinion in International Application No. PCT/GB2017/053735, dated Mar. 14, 2018, 14 pages.
Pelliccia, et al., "Treatment with CBD in oily solution of drug-resistant paediatric epilepsies," Available online Sep. 2, 2010, Retrieved Jun. 30, 2015; http://www.gwpharm.com/uploads/pelliccia-2002-treatmentwithcbdinoilysolutionofdrug-resistantpediatricepilepsies.pdf, Abstract only, 2 pages.
Pereira, et al., "Study pharmacologic of the GABAergic and glutamatergic drugs on seizures and status epilepticus induced by pilocarpine in adult Wistar rats," Neurosci Lett., 419(3):253-7 (2007). Epub Apr. 13, 2007.
Pertwee, "Cannabinoid receptor ligands: clinical and neuropharmacological considerations, relevant to future drug discovery and development," Expert Opin Investig Drugs, 9(7):1553-71 (2000).

(56) References Cited

OTHER PUBLICATIONS

Pertwee, "Chapter 3: The Pharmacology and Therapeutic Potential of Cannabidiol," Cannabinoids, Ed Vincenzo Di Marzo ed., 2004, 32-83.

Pertwee, "The diverse CB1 and CB2 receptors pharmacology of three plant cannabinoids: Alpha9 Tetrahydrocannabinol, cannabidiol and alpha9-tetrahydrocannabivarin," Br. J. Pharmacol. 153 (2): 199-215, 2008.

Petrocellis, et al., "Effects of cannabinoids and cannabinoid-enriched Cannabis extracts on TRP channels and endocannabinoid metabolic enzymes," British Journal of Pharmacology (2011) 163 1479-1494.

Physician's Desk Reference, 63rd Ed., 2009, 423-461, 2192-2194, 2639-2242, 3019-3022, 29 pages.

Pohl, et al. "Effects of flunarizine on Metrazol-induced seizures in developing rats," Epilepsy Res. Sep. 1987;1(5):302-5.

Poortman-Van Der Meer, "A contribution to the improvement of accuracy in the quantitation of THC," Forensic Science International, Apr. 1999, 101(1): 1-8.

Porter et al., "Randomized, multicenter, dose-ranging trial of retigabine for partial-onset seizures," Neurology, 68(15):1197-1204 (2007).

Porter et al., "Report of a parent survey of cannabidiol-enriched cannabis use in pediatric treatment-resistant epilepsy," Epilepsy Behav. Dec. 2013;29(3):574-7.

Potter, "Cannabis Horticulture," Chapter 4, Handbook of Cannabis, ed. Roger G. Pertwee, pp. 65-88 (2014).

Pouton, "Lipid formulations for oral administration of drugs: non-emulsifying, self-emulsifying and 'self-microemulsifying' drug delivery systems," Eur. J. Pharm Sci, 11(Supp. 2): S93-S98 (2000).

Press et al., "Parenteral reporting of response to oral cannabis extracts for treatment of refractory epilepsy," Epilepsy Behav, 45:49-52 (2015).

Pruitt et al., "Ethanol in Liquid Preparations Intended for Children," Pediatrics, 73(3):405-407 (1984).

Raab et al., "Multiple myeloma," Lancet, 374(9686):314-339 (2009).

Rabinski [online], "CBD-A: Cannabidiol Acid Cannabinoid Profile," MassRoots, Jul. 2, 2015, retrieved on Jan. 31, 2018, URL <https://www.massroots.com/learn/can-the-cbd-a-cannabinoid-help-you/>, 4 pages.

Ramantani et al., "Epilepsy in Aicardi—Goutières Syndrome," Official J Eur Paediatric Neurology Society, 18:30-37 (2014).

Rauca et al., "The role of superoxide dismutase and alpha-tocopherol in the development of seizures and kindling induced by pentylenetetrazol—influence of the radical scavenger alpha-phenyl-N-tert-butyl nitrone," Brain Research, 1009(1-2):203-212 (2004).

Resstel et al. "5-HT$_{1A}$ receptors are involved in the cannabidiol-induced attenuation of behavioural and cardiovascular responses to acute restraint stress in rats," Br J Pharmacol., 156(1):181-188 (2009).

Rosenberg et al., "Cannabinoids and Epilepsy," Neurotherapeutics, 12(4):747-768 (2015).

Rosenkrantz et al., "Oral and Parenteral Formulations of Marijuana Constituents," J Pharm Sci, 61(7):1106-1112 (1972).

Rubio et al., "In vivo Experimental Models of Epilepsy," Central Nervous System Agents in Medicinal Chemistry, 10:298-309 (2010).

Russo, "Taming THC: potential cannabis synergy and phytocannabinoid-termoid entourage effects," British J. of Pharm., 163:1333-1364 (2011).

Sadanandasarma et al., "Key Attributes of TKDL: Suddha Bhanga Visista Gunah Aur Matra," Rasatarangini 11th Ed., 720-723 (with English translation), 8 pages.

SalutarisDrops.com [online], "Cannabidiol for Aicardi Syndrome," Salutaris, available on or before Oct. 2014, retrieved on Feb. 10, 2017, URL <http://web.archive.org/web/20141012220050/http://salutarisdrops.corn/cannabidiol-aicardi-syndrome/>, 3 pages.

Sander, "The epidemiology of epilepsy revisited," Curr Opin Neural, 16(2):165-170 (2003).

Sandyk et al., "Preliminary trial of cannabidiol in Huntington's Disease," Marihuana: An International Research Report, 157-162 (1988).

Sastri et al., "Key Attributes of TKDL: Vijaya Kalpah (Apasmaranasaka)," Anandakandam 1st ed., 1952:241 (with English translation), 5 pages.

Scuderi et al., "Cannabidiol in medicine: a review of its therapeutic potential in CNS disorders," Phytother Res., 23(5):597-602 (2009).

Shukla [online], "New Automated Purification Strategies for Scale-Up," PCISyntesis.com, posted Dec. 25, 2017, https://www.pcisynthesis.com/new-automated-purification-strategies-for-scale-up/, 5 pages.

Silva et al., "Position Statement on the Use of Medical Cannabis for the Treatment of Epilepsy in Canada," Can J. Neurol. Sci., 33:783-786 (2006).

Sperling et al., "Carisbamate as adjunctive treatment of partial onset seizures in adults in two randomized, placebo-controlled trials," Epilepsia, 51(3):333-343 (2010).

Stafstrom et al., "Models of Pediatric Epilepsies: Strategies and Opportunities," Epilepsia, 47(8):1407-1414 (2006).

Stephenson, "In Memoriam: Professor Jean Aicardi (1926-2015)," Pediatric Neurology, 54:3-4 (2016).

Stott et al., "Cannabinoids for the pharmaceutical industry," Euphytica, 140:83-93 (2004).

Strickley, "Solubilizing Excipients in Oral and Injectable Formulations," Table VIII, Pharmaceutical Research, 21(2):201-230 (2004).

Swann et al., "The effects of seizures on the connectivity and circuitry of the developing brain," Ment Retard Dev Disabil Res Rev., 10(2):96-100 (2004).

Thomas et al., "Evidence that the plant cannabinoid Delta9-tetrahydrocannabivarin is a cannabinoid CBI and CB2 receptor antagonist," Br J Pharmacol., 146(7):917-926 (2005).

Thomas et al., "Cannabidiol displays unexpectedly high potency as an antagonist of CB1 and CB2 receptor agonists in vitro," British J Pharmacology, 150(5):613-623 (1988).

Thumma et al., "Influence of plasticizers on the stability and release of a prodrug of delta-9 tetrahydrocannabinol incorporated in poly (ethylene oxide) matrices," Eur J Pharmaceutics and Biopharmaceutics, 70(2):605-614 (2008).

Thurman et al., "Standards for epidemiologic studies and surveillance of epilepsy," Epilepsia, 52 (Suppl 7):2-26 (2011).

Thurston, "Avoid Charlotte's Web for Epilepsy," Jun. 26, 2014, URL <http://drthurstone.com/charlotted-web-not-safest-option-epilepsy-treatment/>, 4 pages.

Trembly & Sherman, "Double-blind clinical study of cannabidiol as a secondary anticonvulsant," Marijuana '90 Int. Conf. on Cannabis and Cannabinoids, Kolympari (Crete), Jul. 8-11, 1990, 1 page, Abstract only.

Turkanis et al., "An Electrophysiological Analysis of the Anticonvulsant Action of Cannabidiol on Limbic Seizures in Conscious Rats," Epilepsia., 20:351-363 (1979).

Unimed Pharmaceuticals, Inc., "Marinol®," Jul. 2006, <https://www.accessdata.fda.gov/dmgsatfda docs/label/2006/018651 s025s026lbl.pdf>, 11 pages.

U.S. Department of Health and Human Services, Food and Drug Administration Center for Drug Evaluation and Research (CDER), "Guidance for Industry Estimating the Maximum Safe Starting Dose in Initial Clinical Trials for Therapeutics in Adult Healthy Volunteers," Jul. 2005, 30 pages.

Usami et al., "Synthesis and pharmacological evaluation in mice of halogenated cannabidiol derivatives," Chem Pharm Bull (Tokyo), 47(11):1641-1645 (1999).

USPTO Decision on Appeal in U.S. Appl. No. 10/318,659 (Appeal 2009-011751), dated Jul. 8, 2010, 23 pages.

USPTO Decision on Appeal in U.S. Appl. No. 13/698,730 (Appeal 2016-006358), dated Jun. 21, 2017, 6 pages.

USPTO Information Disclosure Statement Form PTO-1449 for U.S. Appl. No. 13/380,305, dated Nov. 24, 2014, 8 pages.

USPTO Notice of Allowance in U.S. Appl. No. 13/380,305, dated Dec. 10, 2014, 5 pages.

USPTO Notice of Allowance in U.S. Appl. No. 13/380,305, dated Mar. 19, 2015, 7 pages.

USPTO Office Action in U.S. Appl. No. 13/380,305, dated Aug. 25, 2014, 6 pages.

USPTO Request for Continued Examination with Amendment and Information Disclosure Statement in U.S. Appl. No. 13/380,305, filed Mar. 2, 2015, 8 pages.

(56) References Cited

OTHER PUBLICATIONS

USPTO Third Preliminary Amendment in U.S. Appl. No. 13/380,305, dated May 23, 2014, 4 pages.
Utah.gov [online], "2nd Agenda Controlled Substances Advisory Committee Meeting," Nov. 12, 2013, URL <https://www.utah.gov/pmn/files/81459.pdf>, 63 pages.
Van Rijckevorsel, "Treatment of Lennox-Gastaut Syndrome: overview and recent findings," Neuropsychiatr Dis Treat, 4(6):1001-1019 (2008).
Velasco et al., "Anticancer mechanisms of cannabinoids," Curr Oncol, 23(2):S23-S32 (2016).
Velisek, "Chapter 11: Models of Chemically-Induced Acute Seizures," Models of Seizures and Epilepsy, pp. 127-152 (2006).
Veliskova, "Chapter 48: Behavioral Characterization of Seizures in Rats," Models of Seizures and Epilepsy, pp. 601-611 (2006).
Vollner et al., "Haschisch XX+[Haschisc XX+]: Cannabidivarin, a new hashish substance," Tetrahedron Letters, 10(3):145-147 (1969).
Wahle et al., "Development of Tolerance to the Anticonvulsant Effect of Valproate but not to Ethosuximide in a Rat Model of Absence Epilepsy," Eur J Pharma, 181(1-2):1-8 (1990).
Wallace et al., "Pharmacotherapy for Dravet Syndrome," Pediatr. Drugs, 18:197-208 (2016).
Wallace et al., "Assessment of the role of CB 1 receptors in cannabinoid anticonvulsant effects," Eur J Pharmacol., 428(1):51-57 (2001).
Weston et al., "Tetrahydrocannabivarin exhibits anticonvulsant effects in a piriform cortical brain slice model of epileptiform activity," Proceedings of the British Pharm Society, Dec. 2006, retrieved on Mar. 1, 2017, URL <http://www.pA2online.org/abstrat/abstract.jsp?abid=28533>, 1 page, Abstract only.
Wikipedia.org [online], "Cannabinoid," Wikipedia, Apr. 2003, retrieved on Mar. 1, 2017, URL <https://en.wikipedia.org/wiki/Cannabinoid>, 15 pages.
Wingerchuk, "Cannabis for medical purposes: cultivating science, weeding out the fiction," Lancet, 364:315-316 (2004).
Yu et al., "Reduced sodium current in GABAergic interneurons in a mouse model of severe myoclonic epilepsy in infancy," Nature Neuroscience, 9(9):1142-1149 (2006).
Yuriev, "Endogenic cannabinoid system is a new perspective object of pharmacotherapeutic effect to disease of nervous system," Ukrainsky Mnemotechny Chasopis, 6(50):21-29 (2005) (with English Abstract).
Zamberletti et al., "Alterations of prefrontal cortex GABAergic transmission in the complex psychotic-like phenotype induced by adolescent delta-9-tetrahydrocannabinol exposure in rats," Neurobiology of Disease, 63:35-47 (2014).
Zhao et al., "Chapter 27: Repetitive Seizures in the Immature Brain," Models of Seizures and Epilepsy, 341-350 (2006).
Zhornitsky & Potvin, "Cannabidiol in Humans—The Quest for Therapeutic Targets," Pharmaceuticals, 5:529-552 (2012).
Zuardi et al., "Cannabidiol, a Cannabis sativa constituent, as an antipsychotic drug," Braz J Med Biol Res., 39(4):421-429 (2006).
Zuardi et al., "Cannabidiol: from an inactive cannabinoid to a drug with wide spectrum of action," Rev Bras Psiquiatr, 30(3):271-280 (2008).
Pelc et al., "Behavior and neuropsychiatric manifestations in Angelman syndrome," Neuropsychiatric Disease and Treatment, 4(3):577-584 (2008).
Gu et al., "Cannabidiol attenuates seizures and EEG abnormalities in Angelman syndrome model mice," The Journal of Clinical Investigation, 129(12):5462-5467 (2019).
[No Author Listed] Charlotte's Web Certificate of Analysis, Test ID# 10.16.13.a, Analysis Date: Oct. 16, 2013, 1 page.
Rotaru et al., "Angelman Syndrome: From Mouse Models to Therapy," Neuroscience, 445:172-189 (2020).
Shaaya et al., "Seizure treatment in Angelman syndrome: A case series from the Angelman Syndrome Clinic at Massachusetts General Hospital," Epilepsy and Behavior, 60(2016)138-141 (2016).

* cited by examiner

Figure 1: Effect of CBD on clasping duration in a mouse model of Angelman syndrome
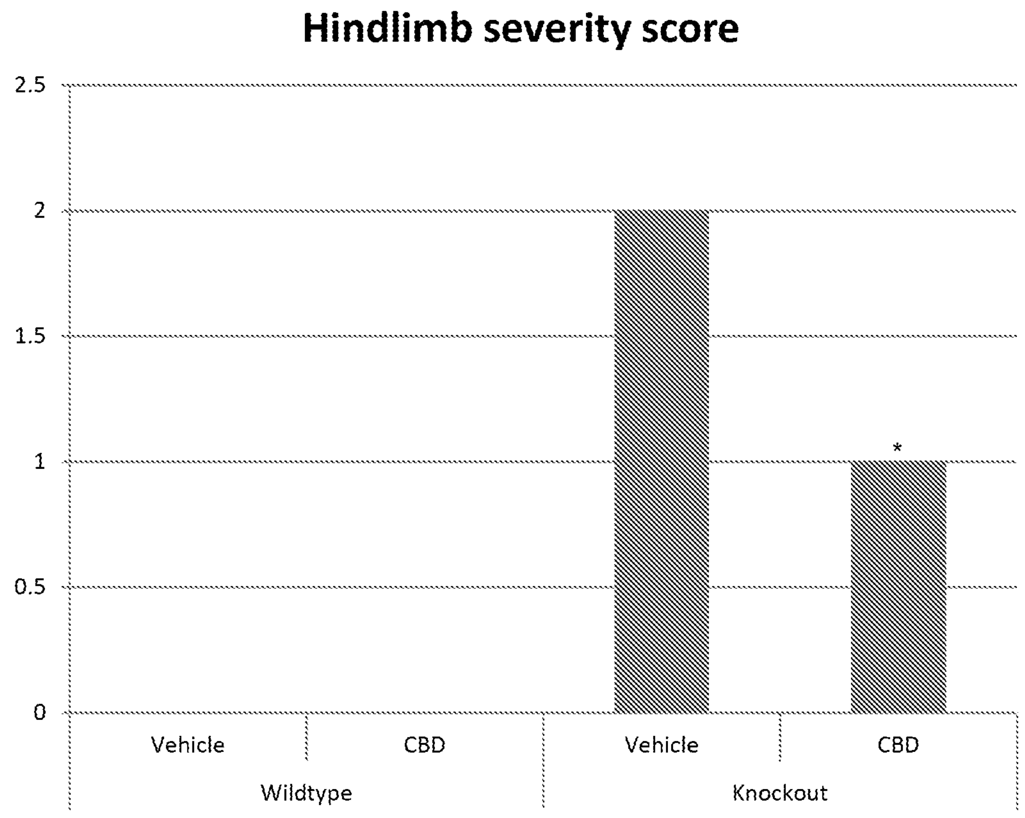

Figure 2: Effect of CBD in the rotarod test in a mouse model of Angelman syndrome
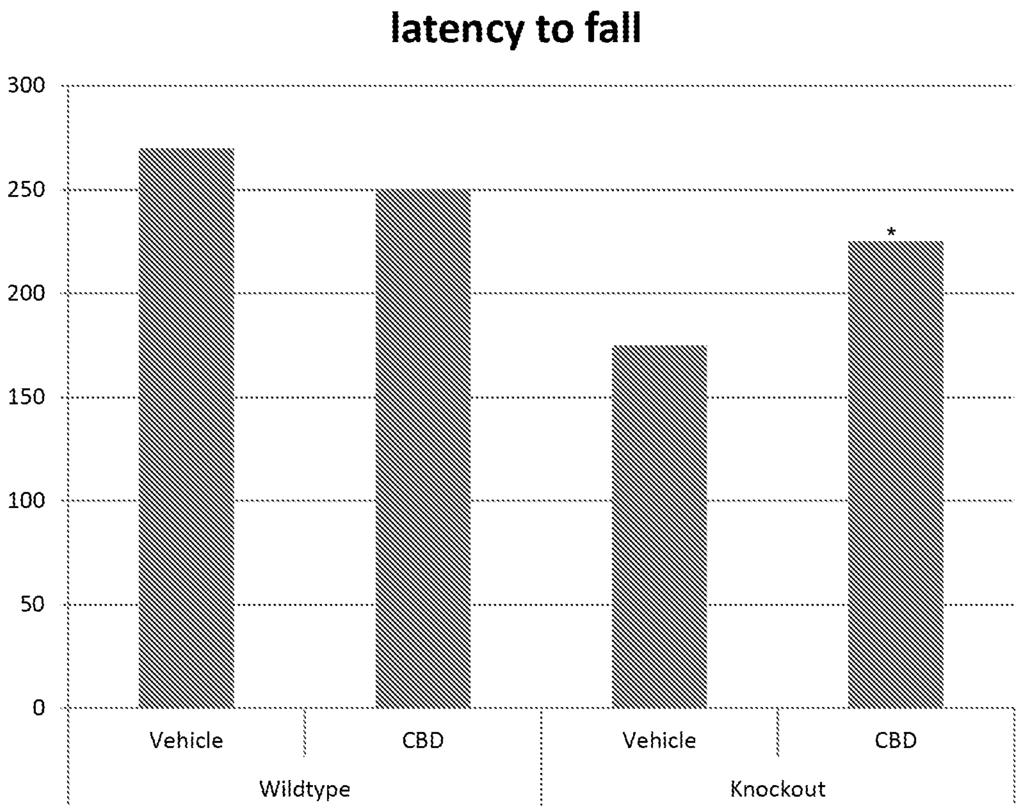

Figure 3: Effect of CBD in the novel object recognition test in a mouse model of Angelman syndrome
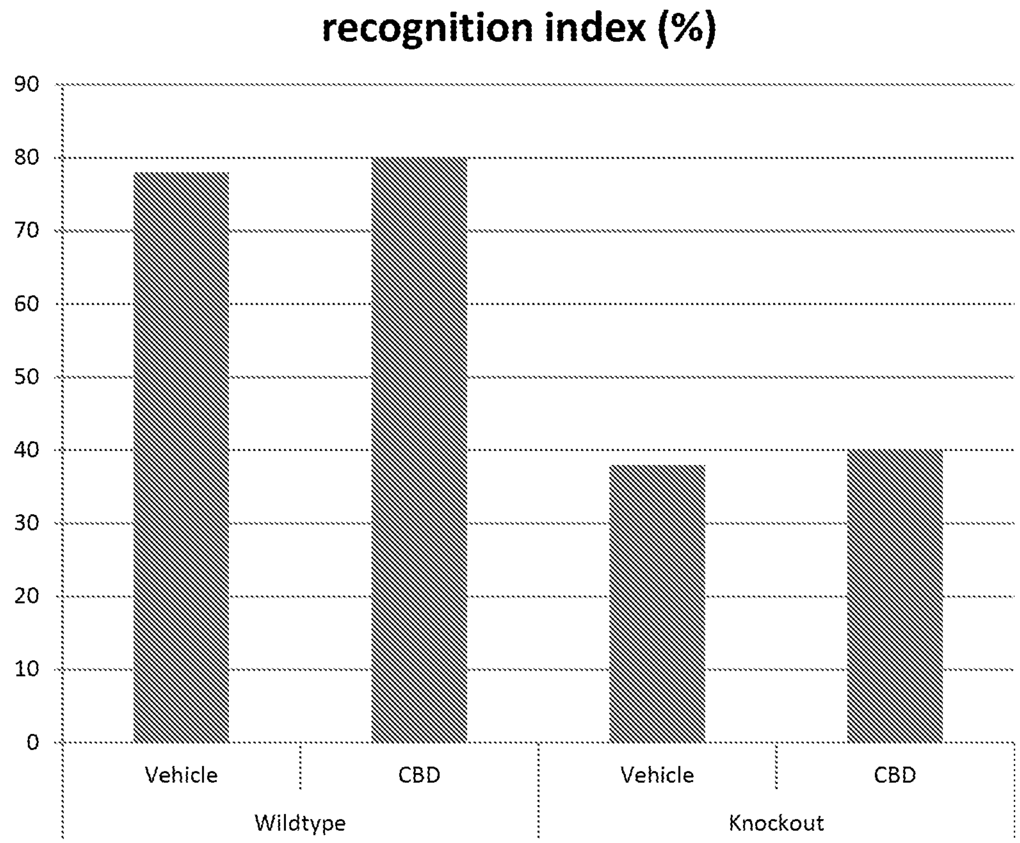

Figure 4: Effect of CBD in the tail suspension test in a mouse model of Angelman syndrome
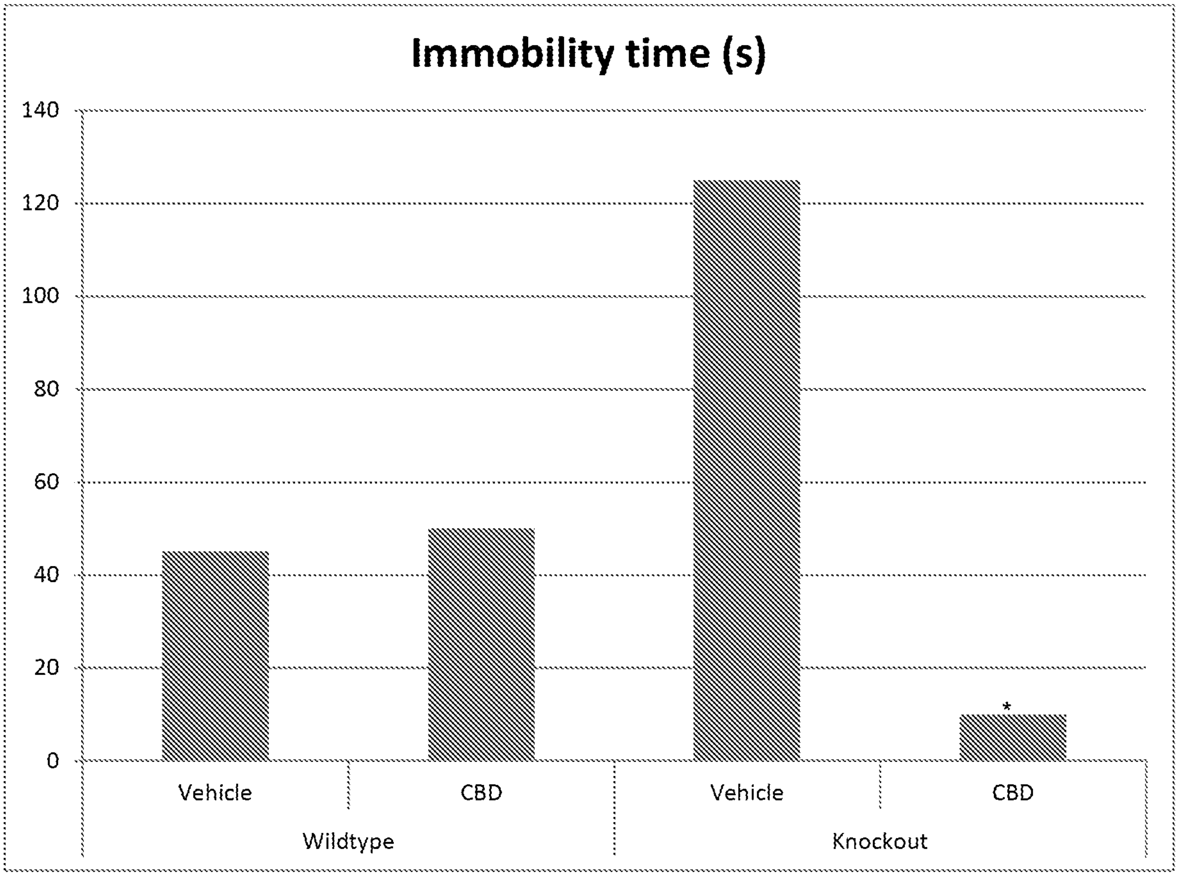

USE OF CANNABINOIDS IN THE TREATMENT OF ANGELMAN SYNDROME

CROSS-REFERENCE TO RELATED APPLICATIONS

This application is a Continuation of application Ser. No. 16/467,639 filed Jun. 7, 2019, now U.S. Pat. No. 11,679,087, which claims the benefit of International PCT Application No. PCT/GB2017/053735 filed Dec. 13, 2017; and Great Britain Application No. 1621480.1 filed Dec. 16, 2016; all of which are incorporated herein by reference to their entirety.

FIELD OF THE INVENTION

The present invention relates to the use of cannabidiol (CBD) in the treatment of Angelman syndrome (AS).

The CBD is preferably substantially pure. It may take the form of a highly purified extract of cannabis such that the CBD is present at greater than 98% of the total extract (w/w) and the other components of the extract are characterised. Alternatively, the CBD is synthetically produced.

In a further alternative the CBD may be used as a botanical drug substance (BDS) from a cannabis plant in which CBD is the predominant cannabinoid. In such an embodiment the CBD may be present in combination with other cannabinoids and non-cannabinoid components such as terpenes.

In use the CBD may be used concomitantly with one or more other medicaments. Alternatively the CBD may be formulated for administration separately, sequentially or simultaneously with one or more medicaments or the combination may be provided in a single dosage form. Where the CBD is formulated for administration separately, sequentially or simultaneously it may be provided as a kit or together with instructions to administer the one or more components in the manner indicated. It may also be used as the sole medication, i.e. as a monotherapy.

BACKGROUND TO THE INVENTION

Angelman syndrome (AS) occurs in approximately 1 in 12,000 to 15,000 individuals and is caused by abnormalities on chromosome 15. Individuals with AS typically show severe to profound learning disability, significant difficulties with mobility and communication in addition to seizures.

It has been suggested that between 50% and 80% of individuals with AS meet the criteria for autism spectrum disorder.

Typical characteristics of Angelman syndrome include: delayed development which is usually noticeable from 6-12 months of age; severe language impairment with little or no speech; movement and balance problems (ataxia); frequent seizures (epilepsy) in around 85% of cases; a small head size (microcephaly); sociable behaviour with frequent smiling.

A genetic anomaly responsible for AS occurs by chance around the time of conception. The UBE3A gene is either absent or malfunctions. A child usually inherits one copy of the UBE3A gene from each parent. Both copies are switched on (active) in most of the body's tissues. However, in certain areas of the brain, only the gene inherited from the mother is active. In most cases of AS (about 70%), the child's maternal copy of the UBE3A gene is missing, which means there's no active copy of the UBE3A gene in the child's brain.

Testing compounds for their effectiveness on signs and symptoms of Angelman syndrome is challenging given that this disorder has so many different affected symptom domains.

The UBE3A mouse model is used to evaluate a compounds effectiveness in the treatment of AS. This model has been shown to recapitulate many of the phenotypic features of AS, including motor dysfunction, increased seizure susceptibility, and hippocampal-dependent learning and memory deficits in mice with the knockout gene.

The NOR test is used to evaluate cognition, particularly recognition memory, in rodent models of CNS disorders, such as Angelman syndrome. The test is based on the tendency of rodents to spend more time exploring a novel object than a familiar one. The choice to explore the novel object reflects the use of learning and recognition memory.

The NOR test is conducted in an open field arena with two different kinds of objects. Both objects are generally consistent in height and volume, but are different in shape and appearance. During habituation, the animals are allowed to explore an empty arena. Twenty-four hours after habituation, the animals are exposed to the familiar arena with two identical objects placed at an equal distance. The next day, the mice are allowed to explore the open field in the presence of the familiar object and a novel object to test short-term and long-term recognition memory. The time spent exploring each object and the discrimination index percentage is recorded. This test is useful for assessing cognitive dysfunction in rodent models of AS.

There is no specific therapy for Angelman syndrome. Medication is usually required to control seizures. Physical and occupational therapies, communication therapy, and behavioral therapies are also important.

The endocannabinoid system has been linked to physiological progression of autism spectrum disorders, possibly implicating CB1 and CB2 receptors.

The phytocannabinoids are known to interact with the endocannabinoid system.

The phytocannabinoid tetrahydrocannabinol (THC) in the form of dronabinol, CB1 agonist, has been used to treat an autistic child (Kurz and Blass, 2010). Problems associated with the use of CB1 agonists are psychoactivity, anxiety and hallucinations.

Patent application WO 2014/146699 describes the use of CB1 receptor antagonists in the treatment of diseases associated with dendritic abnormalities. Such diseases include AS and RS. The application is exemplified by the use of rimonabant in the FMR1 knockout mouse model which is a model of FXS.

The CB1 antagonist, rimonabant, has been shown to have serious side effects which limit its use, such as suicide ideation.

The present application relates to the use of a phytocannabinoid which is neither a CB1 agonist nor antagonist. CBD is known to have a low affinity for the CB1 receptor (Mechoulam et al. 2007).

To date there are no studies of the use of CBD in the treatment of AS. Such symptoms as described above are difficult to treat, therefore many patients with AS have unmet needs with respect to the treatment of their disease.

BRIEF SUMMARY OF THE DISCLOSURE

In accordance with a first aspect of the present invention there is provided Cannabidiol (CBD) for use in the treatment of Angelman syndrome.

In this aspect, treatment of Angelman syndrome encompasses the treatment of the condition as a whole, as opposed to the individual symptoms.

In accordance with a second aspect of the present invention there is provided Cannabidiol (CBD) for use in the treatment of one or more symptoms or characteristics associated with of Angelman syndrome.

Preferably the symptoms or characteristics associated with Angelman syndrome are one or more of: movement disorders; anxiety and/or cognitive dysfunction.

In accordance with a third aspect of the present invention there is provided Cannabidiol (CBD) for use in the treatment of movement disorders associated with Angelman syndrome.

In accordance with a forth aspect of the present invention there is provided Cannabidiol (CBD) for use in the treatment of anxiety associated with Angelman syndrome.

In accordance with a fifth aspect of the present invention there is provided Cannabidiol (CBD) for use in the treatment of cognitive dysfunction associated with Angelman syndrome.

In a further embodiment the CBD is for use in combination with one or more concomitant medicaments which may be taken by the patient to treat the condition and/or one or more symptoms associated therewith. Such as, for example, melatonin for sleeping problems, SSRI for depression, anticonvulsants for epilepsy, methylphenidate for ADHD or antipsychotics for aggression or self-harming behaviour. Preferably the one or more concomitant medicaments is an anti-epileptic drug (AED).

In a preferred embodiment the CBD is substantially pure. The CBD may be present as a highly purified extract of cannabis which comprises at least 98% (w/w) CBD. Preferably the extract comprises less than 0.15% THC.

In an alternative embodiment the CBD is present as a synthetic compound.

In yet a further embodiment the CBD may be used as a botanical drug substance, as an extract from a cannabis plant in which CBD is the predominant cannabinoid. The CBD may also be present in combination with other cannabinoids and non-cannabinoid components such as terpenes.

Determining an effective dose in humans will depend on, for example the mode of delivery (e.g. i.v. or oral), the formulation and the bioavailability of the CBD when delivered and might range between 0.1 and 100 mg/kg/day. Furthermore the fact that cannabinoids often show bell-shaped dose response curves makes determining a dose of CBD more difficult.

Preferably the dose of CBD is greater than 0.1 mg/kg/day. Thus, for a 15 kg patient a dose of greater than 1.5 mg of CBD per day would be provided. Doses greater than 1 mg/kg/day such as greater than 5/mg/kg/day, greater than 10 mg/kg/day, greater than 15 mg/kg/day and greater than 20 mg/kg/day are also envisaged to be effective.

Preferably the CBD is provided over an extended period; more preferably this period is at least seven days.

In a further embodiment the CBD may be used as a dietary supplement or food additive in order to improve symptoms in Angelman syndrome.

In accordance with a sixth aspect of the present invention there is provided a method of treating Angelman syndrome, comprising administering an effective amount of cannabidiol (CBD) to the subject in need thereof.

Preferably the subject is a human.

Preferably the symptoms or characteristics associated with Angelman syndrome are one or more of: movement disorders; anxiety and/or cognitive dysfunction.

In accordance with a seventh aspect of the present invention there is provided a method of treating a movement disorder in an Angelman syndrome subject comprising administering an effective amount of cannabidiol (CBD) to the subject in need thereof.

Preferably the subject is a human.

In accordance with a eighth aspect of the present invention there is provided a method of treating anxiety in an Angelman syndrome subject comprising administering an effective amount of cannabidiol (CBD) to the subject in need thereof.

Preferably the subject is a human.

In accordance with a ninth aspect of the present invention there is provided a method of treating a cognitive disfunction in an Angelman syndrome subject comprising administering an effective amount of cannabidiol (CBD) to the subject in need thereof.

Preferably the subject is a human.

The human equivalent dose (HED) can be estimated using the following formula:

$$HED = \text{Animal dose (mg/kg) multiplied by } \frac{\text{Animal } K_m}{\text{Human } K_m}$$

The $K_m$ for a mouse is 3, for a rat the $K_m$ is 6 and the $K_m$ for a human is 37.

Furthermore when animal data is obtained using an intraperitoneal form of dosing, but the drug is to be administered using a different delivery method, then the HED calculated may need to be adjusted to take account of the different mode of delivery. In the case of an oral dose the HED may need to be increased in order to obtain an equivalent oral dose, depending on the formulation used, mode of delivery and bioavailability of the active. This is something a skilled pharmacologist will recognise.

Definitions

Definitions of some of the terms used to describe the invention are detailed below:

The cannabinoids described in the present application are listed below along with their standard abbreviations.

TABLE 1

| Cannabinoids and their abbreviations | | |
|---|---|---|
| CBD | Cannabidiol | 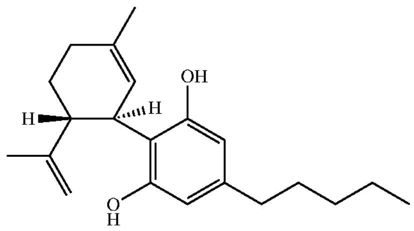 [SMILES: C=C(C)[C@@H]1CCC(C)=C[C@H]1c1c(O)cc(CCCCC)cc1O] |
| THC | Tetrahydrocannabinol | 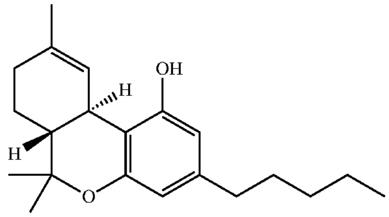 [SMILES: CCCCCc1cc(O)c2c(c1)OC(C)(C)[C@@H]1CCC(C)=C[C@@H]21] |

The table above is not exhaustive and merely details the cannabinoids which are identified in the present application for reference. So far over 60 different cannabinoids have been identified and these cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the cannabis plant. The phytocannabinoids can be isolated from plants to produce a highly purified extract or can be reproduced synthetically.

"Substantially pure CBD" is defined as CBD that is greater than 98% (w/w) pure. More preferably greater than 98.5% (w/w) through 99% (w/w) to 99.5% (w/w) and greater.

"Highly purified cannabinoid extracts" are defined as cannabinoids that have been extracted from the cannabis plant and purified to the extent that other cannabinoids and non-cannabinoid components that are co-extracted with the cannabinoids have been substantially removed, such that the highly purified cannabinoid is greater than or equal to 98% (w/w) pure.

"Botanical drug substance" or "(BDS)" is defined in the Guidance for Industry Botanical Drug Products Draft Guidance, August 2000, US Department of Health and Human Services, Food and Drug Administration Centre for Drug Evaluation and Research as: "A drug derived from one or more plants, algae, or microscopic fungi. It is prepared from botanical raw materials by one or more of the following processes: pulverisation, decoction, expression, aqueous extraction, ethanolic extraction or other similar processes." A botanical drug substance does not include a highly purified or chemically modified substance derived from natural sources. Thus, in the case of cannabis, BDS derived from cannabis plants do not include highly purified Pharmacopoeial grade cannabinoids. In a BDS comprising cannabinoids the cannabinoid will be present in an amount of less than 95% (w/w).

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example it is known that heating the carboxylic acid form will cause most of the carboxylic acid form to decarboxylate into the neutral form.

"Cognitive dysfunction" is defined as the loss of intellectual functions such as thinking, remembering, and reasoning with sufficient severity to interfere with daily functioning. Patients with cognitive dysfunction have trouble with verbal recall, basic arithmetic, and concentration.

BRIEF DESCRIPTION OF THE DRAWINGS

Embodiments of the invention are further described hereinafter with reference to the accompanying drawings, in which FIG. 1 shows the effect of CBD on clasping duration in a mouse model of Angelman syndrome;

FIG. 2 shows the effect of CBD in the rotarod test in a mouse model of Angelman syndrome;

FIG. 3 shows the effect of CBD in the novel object recognition test in a mouse model of Angelman syndrome; and FIG. 4 shows the effect of CBD in the tail suspension test in a mouse model of Angelman syndrome.

Data are expressed as mean±S.E.M. $*p<0.05$, $***p<0.001$ vs WT-vehicle; $^{\circ\circ}p<0.01$, $^{\circ\circ\circ}p<0.001$ vs KO-vehicle. Two-way ANOVA followed by Bonferroni post hoc test.

DETAILED DESCRIPTION

Example 1: Use of Cannabidiol (CBD) in a Mouse Model of Angelman Syndrome

The effect of CBD was tested in the neurological, behavioural and motor disorders in a transgenic mouse model of Angelman Syndrome.

Materials and Methods

Animals

Heterozygous mice with maternal deficiency of Ube3A (Ube3am−/p+) and wild type (Ube3am+/p+) were purchased from The Jackson Laboratory (Jackson code: B6.12957-Ube3a tm1Alb/J) and maintained in a C57BL/6 background.

Animals were housed under controlled illumination (12:12-hour light/dark cycle; light on 6 hours) and environmental conditions (room temperature: 20° C.-22° C., humidity: 55%-60%) with food and tap water were available ad libitum.

Drugs and Treatment

Drugs were dissolved in 1:1:18 ethanol:cremophor: 0.9% saline, for intraperitoneal (i.p.) administration. Drug treatment was performed daily for 35 days. CBD was administered at 20 mg/kg.

Behavioural Tests

Rotarod: The rotarod test assesses balance and motor coordination of mice. Mice have been measured for the time (in seconds) of equilibrium before falling on a rotary cylinder by a magnet that, activated from the fall of the mouse on the plate, allows to record the time of permanence on the cylinder. After a period of adaptation of 30 s, the spin speed gradually increased from 3 to 30 rpm for a maximum time of 5 min. The animals were analysed by 2 separate tests at 1-h interval in the same day.

Clasping: The clasping test assesses ataxia in mice. Mice were suspended by the base of the tail and their behaviours were recorded for 30 seconds. The time for which the mice clasped their hind limbs was recorded. The time was then scored as follows: 4, 15-30 s, 3, 10-15 s, 2, 5-10 s, 1, 0-5 s and 0, 0 s.

Tail suspension: The tail suspension test assesses depressive-like behaviour in mice. Mice were individually suspended by the tail on a horizontal bar (50 cm from floor) using adhesive tape placed approximately 4 cm from the tip of the tail. The duration of immobility was recorded in seconds over a period of 6 minutes by a time recorder. Immobility time was defined as the absence of escape-oriented behaviour.

Novel Object Recognition: The novel object recognition assesses recognition memory in mice. The experiment started with the habituation period, during which mice were allowed to freely explore for 1 hour the apparatus which consists of a rectangular open box (40×30×30 cm width×length×height) made of grey polyvinyl chloride (PVC) illuminated by a dim light. The day after each mouse was allowed to explore two identical objects positioned in the back left and right corners for 5 min (acquisition). A video camera recorded the time spent on exploration of each object. In the test trial, which was carried out for 2 hrs after the acquisition, one of the two objects was replaced with a new different object. The time spent exploring the object was the time that the mouse spent with its nose directed and within 1 cm from the object. The behaviour of mice was analyzed by an observer blind to the treatment. Data are expressed as percentage of recognition index (RI %), which was calculated as the percentage of the time spent exploring the novel object/time spent exploring the novel object+time spent exploring the familiar object×100.

Statistical Analysis: Behavioural data are represented as means±SEM and statistical analysis of these data was performed by two way analysis of variance (ANOVA) for repeated measured followed by the Student Newman-Keuls for multiple comparisons to determine statistical significance between different treated groups of mouse. $p<0.05$ was considered statistically significant.

Results

FIG. 1 shows that AS mice treated with vehicle showed significantly longer clasping duration at 10 weeks of age compared to WT mice treated with vehicle. In AS mice chronic treatment (30 days) with CBD significantly reduced clasping duration at 10 weeks of age compared to AS mice treated with vehicle.

FIG. 2 demonstrates that AS mice treated with vehicle showed a significant motor impairment at 10 weeks of compared to WT mice treated with vehicle. In AS mice, chronic treatment (30 days) with CBD significantly reduced latency to fall compared to AS mice treated with vehicle.

Mice were assessed at the age of 7-8 weeks in the novel object recognition test. AS mice treated with vehicle showed a significant decrease in the discrimination index compared with WT mice that received the same treatment. FIG. 3 shows that AS mice treated with CBD slightly increased the discrimination index compared to AS mice treated with vehicle.

FIG. 4 shows that in the tail suspension test the time of immobility were significantly higher in AS mice that received vehicle compared to WT mice that received the same treatment. In AS mice treatment with CBD significantly reduced the duration of immobility time compared to AS mice treated with vehicle.

Conclusion

These data demonstrate that the treatment of 20 mg/kg CBD to mice which were deficient in the Ube3A gene and subsequently suffered symptoms to individuals with AS, were able to reverse these symptoms. In particular CBD was able to statistically significantly improve movement and balance problems (ataxia) and anxiety. As such CBD is considered to be a viable treatment option for AS.

As is shown in Example 1 above, the use of CBD in a model of Angelman syndrome is able to produce statistically significant reversal of the symptoms associated with this disorder.

In particular CBD has been shown to produce positive results in the Tail Suspension test in this model and as such demonstrates unequivocally that this phytocannabinoid could reverse anxiety in this disorder.

In addition, other tests in this model provide support that CBD could be used to treat additional symptoms associated with this disorder as it was able to reduce ataxia and balance and motor coordination symptoms in a model of Angelman syndrome. As such CBD provides a real treatment option to individuals suffering from AS.

REFERENCES

Hill T et al. (2012) Br J Pharmacol. December; 167(8):1629-42. Cannabidivarin is anticonvulsant in mouse and rat.

Erica Zamberletti, Sarah Beggiato, Luca Steardo Jr., Pamela Prini, Tiziana Antonelli, Luca Ferraro, Tiziana Rubino, Daniela Parolaro. Neurobiology of Disease (2014), Volume 63, Pages 35-47. "Alterations of prefrontal cortex GABAergic transmission in the complex psychotic-like phenotype induced by adolescent delta-9-tetrahydrocannabinol exposure in rats."

Kurz and Blass 2010 Use of dronabinol (delta-9-THC) in autism: A prospective single-case study with an early infantile autistic child. Cannabinoids, 5 (4) 4-6.

Marta Kruk-Slomka, Agnieszka Michalak, Barbara Budzyn'ska, Graz'yna Biala. Pharmacological Reports 66 (2014), 638-646. "A comparison of mecamylamine and bupropion effects on memory-related responses induced by nicotine and scopolamine in the novel object recognition test in mice."

The invention claimed is:

1. A method for treating Angelman syndrome, comprising orally administering to a subject in need thereof a therapeutically effective amount of a cannabidiol (CBD) drug substance, wherein the CBD drug substance comprises at least 98% (w/w) CBD and the CBD is administered at a dose of at least 20 mg/kg/day.

2. The method of claim 1, wherein the CBD drug substance is administered in combination with one or more concomitant medications.

3. The method of claim 1, wherein the CBD drug substance is administered in combination with at least one anti-epileptic drug (AED).

4. The method of claim 1, wherein the CBD drug substance is an extract of cannabis.

5. The method of claim 4, wherein the extract comprises less than 0.15% THC.

6. The method of claim 1, wherein the CBD is a synthetic compound.

7. The method of claim 1, further comprising treating a movement disorder.

8. The method of claim 1, further comprising treating cognitive dysfunction.

9. The method of claim 1, wherein the CBD drug substance comprises greater than 98.5% (w/w) CBD.

10. The method of claim 9, wherein the CBD is an extract of cannabis.

11. The method of claim 9, wherein the CBD is a synthetic compound.

12. The method of claim 1, wherein the CBD drug substance comprises greater than 99% (w/w) CBD.

13. The method of claim 12, wherein the CBD is an extract of cannabis.

14. The method of claim 13, wherein the extract comprises less than 0.15% THC.

15. The method of claim 1, wherein the treating Angelman syndrome comprises treating anxiety in Angelman syndrome.

* * * * *